United States Patent [19]

Barriere et al.

[11] Patent Number: 4,798,827
[45] Date of Patent: Jan. 17, 1989

[54] SYNERGISTIN DERIVATIVES AND PHARMACEUTICAL COMPOSITIONS WHICH CONTAIN THEM

[75] Inventors: Jean-Claude Barriere, Massy; Claude Cotrel, Paris; Jean-Marc Paris, Vaires sur Marne, all of France

[73] Assignee: Rhone-Poulenc Sante, Courbevoie, France

[21] Appl. No.: 52,371

[22] Filed: May 21, 1987

[30] Foreign Application Priority Data

May 22, 1986 [FR] France .................... 86 07270

[51] Int. Cl.$^4$ .............. A61K 37/02; A61K 31/42; C07K 5/12; C07D 498/14
[52] U.S. Cl. .................... 514/183; 514/11; 530/317; 540/455
[58] Field of Search .............. 514/183; 540/455

[56] References Cited

U.S. PATENT DOCUMENTS

| 4,617,290 | 10/1986 | Corbet et al. | 514/11 |
| 4,617,377 | 10/1986 | Corbet et al. | 530/317 |
| 4,618,599 | 10/1986 | Corbet et al. | 514/11 |
| 4,668,669 | 5/1987 | Barriere et al. | 540/455 |

FOREIGN PATENT DOCUMENTS

| 0133097 | 2/1985 | European Pat. Off. | 514/183 |
| 0133098 | 2/1985 | European Pat. Off. | 540/455 |
| 0133096 | 2/1985 | European Pat. Off. | 514/11 |

OTHER PUBLICATIONS

Chemical Abstracts, vol. 103, (1985), Item 160861e, Abstracting French Demande FR 2,549,065, Jan. 18, 1985.
Chemical Abstracts, vol. 103, (1985), Item 160862f, Abstracting French Demande FR 2,549,063.

*Primary Examiner*—Robert T. Bond
*Attorney, Agent, or Firm*—Stevens, Davis, Miller & Mosher

[57] ABSTRACT

The invention provides new synergistin derivatives of formula

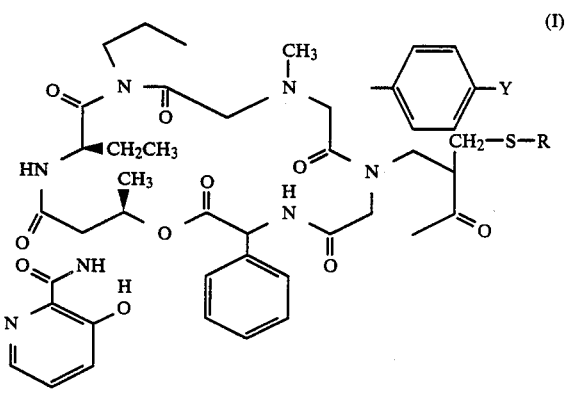

in which Y is hydrogen or dimethylamino and R is a 3- or 4-quinuclidinyl radical, the isomers thereof and their mixtures, and their salts, also the preparation thereof. These compounds may be made by reaction of the corresponding 5-methylene compounds with the appropriate mercaptoquinuclidine. The products of formula (I), optionally combined with pristinamycin II$_A$ or a derivative of pristinamycin II$_B$ of the formula

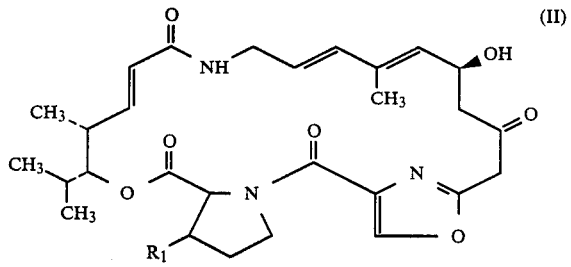

are useful as antimicrobials.

7 Claims, No Drawings

SYNERGISTIN DERIVATIVES AND PHARMACEUTICAL COMPOSITIONS WHICH CONTAIN THEM

This invention relates to synergistic derivatives, their preparation, and pharmaceutical compositions containing them.

European patent application EP No. 133,097 describes synergistin derivatives substituted at the 5δ-position which have the advantage of being soluble.

Pristinamycin and virginiamycin are known compounds: J. Preud'homme et al., Bull. Soc. Chim. Fr., 2, 585–91 (1968).

The present invention provides new synergistin derivatives of the formula:

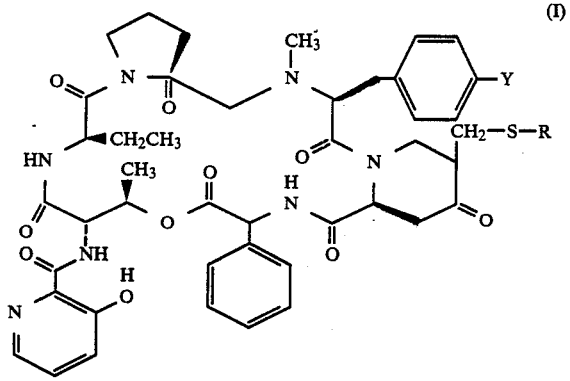

in which Y is hydrogen or dimethylamino and R is 3- or 4-quinuclidinyl, and their salts. The compounds of formula (I) exist in isomeric forms and these isomers and mixtures thereof are within the scope of the invention.

According to a feature of the invention, the compounds of formula (I) in which Y and R are as defined above, are prepared by the reaction of a thiol of formula:

R—SH  (II)

in which R is as defined above, with a compound of formula:

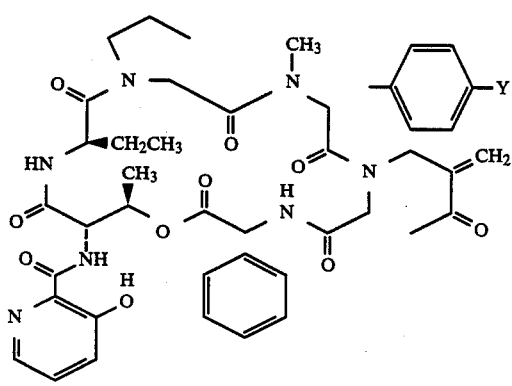

in which Y is as defined above.

The reaction is generally performed in an organic solvent such as an alcohol, (e.g. methanol), a ketone (e.g. acetone) or a chlorinated solvent (e.g. chloroform), or in a mixture of such solvents, at a temperature between −78° C. and the reflux temperature of the reaction mixture, preferably at about 20° C.

When the symbol R denotes 3-quinuclidinyl, it is to be understood that the thiol of formula II of (R) or (S) configuration leads to the synergistin derivative of formula (I) of the corresponding configuration.

The thiol of formula (II) in which R is 3-quinuclidinyl may be obtained from a thiol ester of formula:

R—S—COR'  (IV)

in which R is as defined above and R' is alkyl of 1 to 4 carbon atoms, preferably methyl, by any known method for obtaining a thiol from a thiol ester without affecting the remainder of the molecule. The reaction may be performed, in particular, by alcoholysis in an alkaline medium, e.g. in an alcohol such as methanol, in the presence of sodium methylate or sodium hydroxide, at a temperature from 20° C. to the reflux temperature of the reacton medium.

The thiol ester of formula (IV) may be prepared by analogy with the method described by R. P. Volante, Tet. Let. 22 (33), 3119 (1981) starting with an alcohol of formula:

R—OH  (V)

in which R is as defined above, and a thiocarboxylic acid of formula:

R'—CO—SH  (VI)

in which R' is as defined above, by treatment with a mixture of triphenylphosphine and a dialkyl azodicarboxylate, e.g. diisopropyl azodicarboxylate. The reaction is performed under conditions similar to those described in the above reference.

The alcohol of formula (V) of (R) or (S) form leads to the thiol ester of general formula (IV) of (S) or (R) configuration, respectively.

The alcohol of general formula (V) of (R) or (S) form may be prepared according to the method described by B. RINGDAHL et al., Acta. Pharm. Suec. 16, 281 (1979).

The thiol of general formula (II) in which R is a 4-quinuclidinyl radical may be obtained by the method described by A. Grob, Helv. Chim. Acta, 57, 2339 (1974).

The products of formula (III) may be prepared as described in U.S. Pat. No. 4,617,377.

When the products of formula (I) take the form of a mixture of isomers, it is possible to separate the latter by any known method which does not adversely affect the molecule; e.g. by high performance liquid chromatography.

The products of formula (I) may be purified by the customary known methods, such as crystallization, chromatography, or successive extractions in acidic and basic medium. Since, as is known in the art, synergistins are sensitive to alkaline media, the term "basic medium", as used in this context, means a medium which is just sufficiently alkaline to liberate the parent substance from its acid addition salts, i.e. a medium whose pH does not exceed 7.5 to 8.

The products of formula (I) may be converted into acid addition salts by the action of acids in an organic solvent such as an alcohol, a ketone, an ester or a chlorinated solvent. The salt precipitates, where appropriate after concentrating a solution thereof. It may be separated by filtration or decantation. The acid addition salts may also be obtained as aqueous solutions, by adding an aqueous solution of the corresponding acid to the product of formula (I).

Synergistins obtained by fermentation are greatly in demand in the medical profession for the treatment of many conditions caused by Gram-positive bacteria (e.g. Staphylococcus, Streptococcus, Pneumococcus or Enterococcus) and Gram-negative bacteria (e.g. Haemophilus, Gonococcus or Meningococcus). However, such synergistins have the disadvantage of being insoluble in aqueous media, and they can hence only be administered orally, generally in the form of gelatin capsules, dragees or tablets. As a result of this insolubility, it is impossible to use the known synergistins when the patient is not able to swallow. This is, in particular, the case in paediatrics and resuscitation, whereas the activity spectrum of the synergistins would indicate them as drugs of great value in a large number of circumstances, e.g. in cases of comatose septicaemia.

The new products according to the invention have the considerable advantage of being soluble in water, as their salts, at therapeutically usable doses, while preserving the general activity spectrum of the synergistin. They are active, in particular, against *Staphylococcus aureus* Smith in vitro at concentrations of between 1 and 125 μg/ml and in vivo at doses of between 5 and 50 mg/kg subcutaneously in mice.

In addition, they are especially valuable on account of their low toxicity. Their $LD_{50}$ is generally greater than 150 mg/kg in mice subcutaneously.

The products according to the present invention exhibit, in addition, a phenomenon of synergy when they are used in combination with pristinamycin $II_A$ or a soluble derivative of pristinamycin $II_B$ of formula:

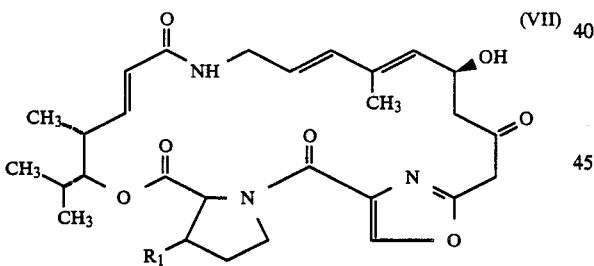

(VII)

in which $R_1$ denotes
(1) an alkylthio radical containing 1 to 5 carbon atoms, substituted by
 (i) one or two alkylamino or dialkylamino radicals in which the alkyl portions, which contain 1 to 5 carbon atoms each, can optionally form, together with the nitrogen atom to which they are attached, a saturated heterocyclic system chosen from 1-pyrrolidinyl, piperidino, 1-azetidinyl, 1-azepinyl, morpholino, thiomorpholino and 1-piperazinyl (optionally substituted by alkyl of 1 to 5 carbon atoms); or alternatively
 (ii) a 2- or 3-pyrrolidinyl, 2-, 3- or 4-piperidyl, 2- or 3-azetidinyl or 2-, 3- or 4-azepinyl radical,
(2) a radical of formula:

Het—S—  (VIII)

in which Het denotes a 3-pyrrolidinyl, 3- or 4-piperidyl, 3-azetidinyl or 3- or 4-azepinyl radical, optionally substituted by alkyl of 1 to 5 carbon atoms;
(3) a dialkylamino radical in which the alkyl portions, which contain 1 to 5 carbon atoms, can optionally form, together with the nitrogen atom to which they are attached, a saturated heterocyclic system chosen from 1-pyrrolidinyl, piperidino, 1-azetidinyl, 1-azepinyl, morpholino, thiomorpholino and 1-piperazinyl (optionally substituted by alkyl of 1 to 5 carbon atoms); or
(4) a radical of general formula:

(IX)

in which $R_2$ denotes
(i) either a 4- to 7-membered nitrogen-containing heterocyclic radical, optionally containing one or more other hetero atoms chosen from nitrogen, oxygen and sulphur in the sulphoxide or sulphone state, and optionally substituted by alkyl;
(ii) or an alkyl chain containing 2 to 4 carbon atoms and substituted by one or two radicals chosen from phenyl, cycloalkylamino and N-alkyl-N-cycloalkylamino containing 3 to 6 ring atoms, alkylamino, dialkylamino or dialkylcarbamoyloxy (the alkyl portions of the latter 2 radicals optionally being able to form, with the nitrogen atom to which they are attached, a 4- to 7-membered saturated or unsaturated heterocyclic system optionally containing another hetero atom chosen from nitrogen, oxygen and sulphur in the sulphoxide or sulphone state, and optionally substituted by alkyl), or substituted by one or more 4- to 7-membered nitrogen-containing heterocyclic radicals optionally containing one or two other hetero atoms chosen from nitrogen, oxygen and sulphur in the sulphoxide or sulphone state, the heterocyclic radicals being optionally substituted by alkyl, and the said heterocyclic radicals being attached to the chain on which they are carried via a carbon atom, with the proviso that at least one of the substituents carried by the above alkyl chain is a nitrogen-containing substituent capable of forming salts;
(iii) or a [(S)-1-methyl-2-pyrrolidinyl]methyl radical and n is 1 or 2, the alkyl radicals mentioned above being linear or branched and containing, except where otherwise stated, 1 to 10 carbon atoms each.

The pristinamycin $II_B$ derivatives of general formula (VII) can exist in isomeric form. These isomeric forms, and mixtures thereof, may be advantgeously combined with the products of formula (I).

In formula (VII), section (4):
when $R_2$ denotes a heterocyclic radical, this radical may be, by way of examle, 3-azetidinyl, 3-pyrrolidinyl, 3- or 4-piperidinyl or 3- or 4-azepinyl;
when $R_2$ denotes an alkyl radical bearing a heterocyclic substituent, the heterocyclic radical may be, by way of example, one of the radicals mentioned above or 2-azetidinyl, 2-pyrrolidinyl, 2-piperidyl, 2-azepinyl, piperazinyl, 4-alkylpiperazinyl, quinolyl, isoquinolyl or imidazolyl;
when $R_2$ contains a dialkylamino or dialkylcarbamoyloxy radical in which the alkyl portions form a heterocyclic system with the nitrogen atom to which they are attached, the heterocyclic radical may be, by way of example, 1-azetidinyl, 1-pyrrolidinyl, piperidino, 1-azepinyl, morpholino, thiomorpholino in the sulphoxide or sulphone state, 1-piperazinyl, 4-alkyl-1-piperazinyl, N-alkyl-1-homopiperazinyl or 1-imidazolyl.

The products of formula (VII) in which $R_1$ is as defined above at sections (1), (2) and (3) form the subject of U.S. Pat. No. 4,590,004, and may be prepared from pistinamycin $II_A$ by the method described in that patent application.

The products of general formula (VII) in which $R_1$ is defined as above at Section (4) may be prepared by oxidation of a pristinamycin $II_B$ derivative, of a salt or protected derivative thereof, of formula:

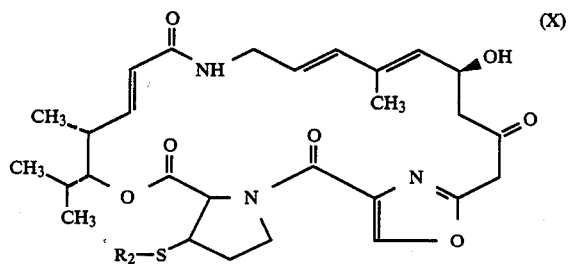

in which $R_2$ is as defined above, with the proviso that, where $R_2$ contains a sulphur-containing heterocyclic system, the sulphur atom can be in the sulphide, sulphoxide or sulphone state.

The reaction is generally accomplished by means of an oxidizing agent, optionally prepared in situ, in aqueous medium or in an organic solvent, preferably a chlorinated solvent (e.g. methylene chloride, 1,2-dichloroethane or chloroform) or an alcohol (e.g. methanol or tert-butanol) or a mixture of these solvents. The reaction is optionally performed under nitrogen.

Among the oxidizing agents which are suitable for obtaining a product of formula (VII) in which n=1, there may be mentioned organic peracids, such as percarboxylic or persulphonic acids (e.g. peracetic, pertrifluoroacetic, performic, perbenzoic, m-chloroperbenzoic, p-nitroperbenzoic, permaleic, monoperphthalic, percamphoric or p-toluenepersulphonic acid) or inorganic peracids (e.g. periodic or persulphuric acid).

When it is desired to obtain a product of formula (VII) in which n=2, the reaction is advantageously performed by the action of selenium dioxide and hydrogen peroxide on a salt of the compound of formula (X), or by the action of a peracid such as those mentioned above, in particular pertrifluoroacetic acid or m-chloroperbenzoic acid.

When the pristinamycin $II_B$ derivative of formula (X) is employed in salt form, a salt formed with an organic or inorganic acid, perferably with trifluoroacetic, tertaric, acetic, benzoic or hydrochloric acid, is used.

When the compound of formula (X) is used in the form of a salt or a protected derivative, the reaction is advantageously performed at a temperature of between −40° and 50° C.

When it is desired to obtain a product of formula (VII) in which n=1, it is also advantageous to use a pristinamycin $II_B$ derivative of formula (X) in the presence of an alkali metal bicarbonate (e.g. sodium bicarbonate) at a temperature of between −60° and −40° C.

When $R_2$ contains an alkylamino or cycloalkylamino substitutent, it is also possible to employ a protected derivative of the product of formula (X). The latter can be protected with any amine-protecting group whose introduction and removal do not affect the remainder of the molecule. Advantageously, the trifluoroacetyl group is used. This can be removed after the reaction by treatment with an alkali metal bicarbonate (e.g. sodium or potassium bicarbonate) in aqueous solution.

The product of formula (X) may be prepared by the action of a thiol of formula:

$$R_2-SH \qquad (XI)$$

in which $R_2$ is as defined above, on pristinamycin $II_A$, by analogy with the method described in European patent application published under No. 135,410.

The products of the formula (VII) in which n is 2 may also be prepared by oxidation of a product of general formula (VII) in which n is 1. The reaction is performed under conditions similar to the conditions described above for obtaining a product of formula (VII) in which n=2, starting with a pristinamycin $II_B$ derivative of general formula (X).

The products of general formula (XI) may be prepared according to, or by analogy with, the methods described below in the Examples, and in particular according to the methods described by:

G. G. Urquart et al., Org. Synth., 21, 36 (1941);
A. I. Vogel, J. Chem. Soc., 1822 (1948);
J. H. Chapman and L. N. Owen, J. Chem. Soc., 579 (1950);
H. R. Snyder et al., J. Am. Chem. Soc., 69, 2672 (1947);
D. D. Reynolds et al., J. Org. Chem., 26, 5125 (1961);
J. W. Haeffele et al., Proc. Sci. Toilet Goods Assoc., 32, 52(1959);
H. Barrer et al., J. Org. Chem., 27, 641 (1962); and
J. H. Biel et al., J. Amer. Chem. Soc., 77, 2250 (1955)

Where appropriate, the isomers of the products of formula (VII) may be separated by chromatography or by high performance liquid chromatography.

The synergistin derivatives according to the present invention have a synergistic effect on the antibacterial action of pristinamycin $II_A$ on *Staphylococcus aureus* Smith in vitro at doses of between 0.1 and 10 µg/cc and in vivo in mice at doses of between 10 and 200 mg/kg subcutaneously, when they are combined in proportions varying between 10–90% and 90–10%.

For therapeutic application, the new products according to the invention may be used as they are, i.e. in the state of the base, but, for use in aqueous solution, this representing an important advantage of the products according to the invention, it is especially advantageous to use their pharmaceutically acceptable salts, that is to say salts which are non-toxic at the doses employed, preferably in combination with pristinamycin $II_A$ or with a soluble derivative of pristinamycin $II_B$ of formula (VII) which is itself dissolved either as a pharmaceutically acceptable salt or, where appropriate, as the base when the solubility is sufficient for the solution obtained to contain an amount of product at least equal to the therapeutically active dose.

As pharmaceutically acceptable salts, there may be mentioned the addition salts with inorganic acids, such as hydrochlorides, hydrobromides, sulphates, nitrates or phosphates, or with organic acids, such as acetates, propionates, succinates, maleates, fumarates, methanesulphonates, p-toluenesulphonates, isethionates, citrates, adipates, lactobionates or substitution derivatives of these compounds.

The Examples which follow show how the invention may be put into practice. The NMR spectra of the products illustrated in these Examples and in the reference Examples show general characteristics which are common to all the products of the general formula (I) or of general formula (VII), and particular characteristics which are specific to each of the products depending on the substituents.

In the Examples which follow, only the particular characteristics due to the variable radicals are mentioned. All the protons are designated according to the numbering shown in the general formula (XII) and recommended by J. O. ANTEUNIS et al. [Eur. J. Biochim., 58, 259 (1975)].

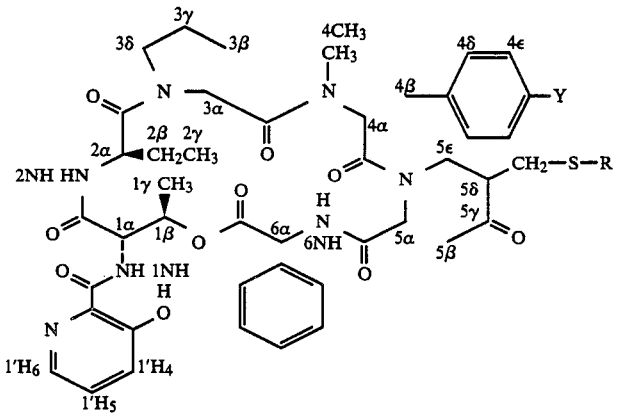

(XII)

For the products of the general formula (VII), all the protons are designated according to the numbering shown in the following formula:

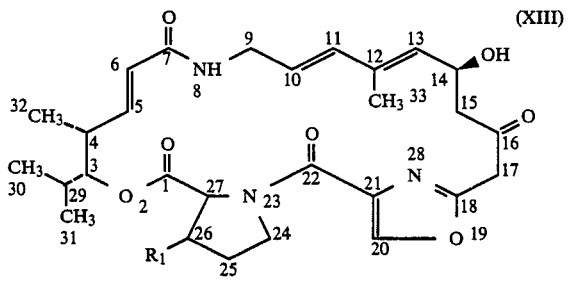

(XIII)

Except where otherwise stated, the spectra were recorded at 250 MHz in deuterochloroform; the chemical shifts are expressed in ppm relative to the tetramethylsilane signal. The abbreviations used below are as follows:
s=singlet
d=doublet
t=triplet
m=multiplet
c=complex
dd=doublet of doublets
dt=doublet of triplets
ddd=doublet of doublets of doublets
dddd=doublet of doublets of doublets of doublets.

It is understood that the different isomers have been classified arbitrarily according to the chemical shifts observed in NMR.

The designations isomer $A_1$ and isomer $A_2$ of the products of general formula (XIII) in which $R_1$ is a radical $R_2S(O)_n$— for which n=1 refer to the isomers which show the following characteristics: approximately 1.7 (s, 13 $CH_3$ at 33); approximately 3.8 (s, >$CH_2$ at 17); <5 (d, $H_{27}$) isomer $A_2$ or >5 (d, $H_{27}$) isomer $A_1$; approximately 5.50 (broad d, $H_{13}$); approximately 6.20 (d, $H_{11}$); approximately 6.6 (>NH at 8); $\geq 8$ (s, $H_{20}$).

The designations isomer $B_1$ and isomer $B_2$ of the products of general formula (XIII) in which $R_1$ is a radical $R_2S(O)_n$— for which n=1 refer to the isomers which show the following characteristics: approximately 1.5 (s, —$CH_3$ at 33); approximately 3.7 and 3.9 (2d, >$CH_2$ at 17); approximately 4.8 (m, $H_{13}$); <5 (d, $H_{27}$) isomer $B_2$ or >5 (d, $H_{27}$) isomer $B_1$; approximately 5.70 (limiting AB, $H_{11}$ and $H_{10}$); approximately 7.7 (>NH at 8); approximately 7.8 (s, $H_{20}$).

The designation isomer A of the product of formula (XIII) in which $R_1$ is other than $R_2S(O)_n$— refers to the isomer which shows NMR characteristics identical to those stated above for the isomers $A_1$ and $A_2$ of the products of the general formula (XIII) in which $R_1$ is a radical $R_2S(O)_n$—, with the proviso that the H at 27 is characterized by: approximately 4.7 (d, $J \leq 1$ Hz).

The designation isomer B of the product of formula (XIII) in which $R_1$ is other than $R_2S(O)_n$ refers to the isomer which shows NMR characteristics identical to those stated above for the isomers $B_1$ and $B_2$ of the products of the formula (XIII), with the proviso that the H at 27 is characterized by: approximately 4.6 (d, $J \geq 2.5$ Hz).

In the examples which follow, flash chromatography refers to a purification technique, the characteristic feature of which is that it is performed under moderate pressure (50 kPa) using a silica of particle size 40–53 μm, according to W. C. STILL, M. KAHN and A. MITRA [J. Org. Chem., 43, 2923 (1978)].

In the Examples below, except where otherwise stated, all the products may be dissolved in water as the hydrochlorides in a concentration of at least 2% by weight.

EXAMPLE 1

3-Mercaptoquinuclidine (2.8 g) is added to a solution of 5δ-methylenepristinamycin $I_A$ (4.4 g) in a mixture of methanol (40 cc) and chloroform (20 cc), and the solution obtained is then stirred for 44 hours at a temperature in the region of 20° C. The reaction mixture is then concentrated to dryness under reduced pressure (2.7 kPa) at 30° C. The residue obtained is suspended in ethyl ether (100 cc) and then separated by filtration. The solid thereby obtained is washed with ethyl ether (3×10 cc) and then purified by flash chromatography [eluant: methylene chloride/methanol (90:10 by volume)], collecting 100-cc fractions. The fractions 11 to 35 are combined and then concentrated to dryness under reduced pressure (2.7 kPa) at 30° C. The residue is stirred in ethyl ether (120 cc). The solid obtained is separated by filtration and then purified again by flash chromatography [eluant: methylene chloride/methanol (85:15 by volume)], collecting 100-cc fractions. Fractions 3 to 7 are combined and then concentrated to dryness under reduced pressure (2.7 kPa) at 30° C. The residue is stirred in ethyl ether (50 cc) and the solid thereby obtained separated by filtration, washed with ethyl ether (3×5 cc) and then dried under reduced pressure (27 Pa) at 20° C. 5δ-[(3-Quinuclidinyl)thiomethyl]pristinamycin $I_A$ (1.7 g) is thereby obtained in the form of a pale yellow solid, m.p. about 200° C.

NMR spectrum: Mixture of 4 isomers: 2.88 and 2.89 (2s, 4—N(CH$_3$)$_2$), 3.21 and 3.22 (2s, 4 —CH$_3$), 6.51 and 6.53 (2d, 2 '—NH—), 6.57 and 6.58 (2d, 4ε), 7.82 and 7.85 (m, the H$_6$ of the 2 preponderant isomers), 7.95 (m, the H$_6$ of the 2 minority isomers), 8.78 and 8.81 (2d, 6 —NH— of 2 preponderant isomers), 8.98 and 9.0 (2d, 6 —NH— of the 2 minority isomers).

A 5% strength aqueous solution of 5δ-[(3-quinuclidinyl)thiomethyl]pristamycin $I_A$ is obtained with:
product: 100 mg
0.1N hydrochloric acid: 0.98 cc
distilled water: 2 cc.

3-Mercaptoquinuclidine may be prepared in the following manner:

Sodium methylate (0.5 g) is added to a solution of 3-(acetylthio)quinuclidine (14.5 g) in methanol (150 cc). The reaction mixture is then heated under reflux for 1 hour. Sodium methylate (0.5 g) is added again and the mixture is then heated under reflux for 2 hours. The reaction mixture is concentrated to dryness under reduced pressure (2.7 kPa) at 40° C. Distilled water (40 cc) is added to the residue obtained, followed by acetic acid (approximately 1 cc) to obtain a pH in the region of 8. The mixture obtained is extracted with methylene chloride (3×20 cc). The combined organic phases are dried over sodium sulphate, filtered and then concentrated to dryness under reduced pressure (2.7 kPa) at 30° C. The brown oil obtained is distilled under reduced pressure (920 Pa); the fraction distilling at about 94° C. is collected. 3-Mercaptoquinuclidine (2.8 g) is thereby obtained.

3-(Acetylthio)quinuclidine may be obtained in the following manner:

Diisopropyl azodicarboxylate (31.6 cc) is added dropwise in the course of 30 minutes to a solution, maintained at 5° C. under an atmosphere of nitrogen, of triphenylphosphine (42 g) in tetrahydrofuran (300 cc). The suspension obtained in then stirred for 30 minutes at 5° C. A solution of 3-hydroxyquinuclidine (10.2 g) and thiolacetic acid (11.4 cc) in tetrahydrofuran (600 cc) is then added to this suspension, maintained at 5° C., in the course of 30 minutes. The reaction mixture is then stirred for 20 hours at a temperature in the region of 20° C. It is then concentrated to dryness under reduced pressure (2.7 kPa) at 40° C. The oil obtained is dissolved in ethyl ether (400 cc), and then washed with hydrochloric acid (3×160 cc). The combined aqueous phases are washed with ethyl ether (100 cc) and then neutralized to a pH in the region of 7 by adding sodium bicarbonate. The pH of the solution obtained is then adjusted to about 9 by adding a few drops of 10N aqueous sodium hydroxide solution. The mixture is extracted with methylene chloride (3×200 cc). The combined organic phases are dried over sodium sulphate, filtered and concentrated to dryness under reduced pressure (2.7 kPa) at 30° C. 3-(Acetylthio)quinuclidine (14.7 g) is thereby obtained in the form of a brown oil [Rf=0.33; eluant: methylene chloride/methanol (90:10 by volume)].

EXAMPLE 2

Working in a manner similar to that described in Example 1, but starting with 5δ-methylenepristinamycin $I_A$ (6.15 g) and (3s)-3-mercaptoquinuclidine (1.1 g) and after two purifications by flash chromatography, collecting 50-cc fractions [1st flash chromatography: eluant: methylene chloride/methanol (90:10 by volume), concentration to dryness of the fractions 12 to 36; 2nd flash chromatography: eluant: methylene chloride/methanol (90:10 by volume), concentration to dryness of the fractions 3 to 20], 5δ-{[(3S)-3-quinuclidinyl]thiomethyl}pristinamycin $I_A$ (2.6 g) is obtained in the form of a pale yellow powder. This product may be obtained in the crystallized state in the following manner: 5δ-{[(3S)-3-Quinuclidinyl]thiomethyl}pristinamycin $I_A$ (2.6 g) is dissolved in methanol (20 cc). A yellow solution is obtained. After filtration and drying under reduced pressure (27 Pa) at 30° C., a crystalline precipitate appears after priming by scratching. 5δ{[(3S)-3-Quinuclidinyl]thiomethyl}pristinamycin $I_A$ (1.2 g) is obtained in the form of white crystals, m.p. about 200° C. (product crystallized in combination with methanol).

NMR spectrum; 1 isomer (traces of the isomer in respect of the 5δ carbon): 0.62 (dd, J=15 and 6, 1H, 5β$_2$), 1.6 to 2.30 (m, 6H,

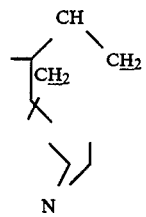

and 5δ), 2.4 (d, J=15, 1H, 5β$_1$), 2.5 to 2.75 (m, 5ε$_2$, 1H of

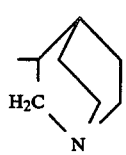

and 1H of —CH$_2$S—), 2.9 to 3.20 (m, —S—CH<, 1H of —CH$_2$S— and

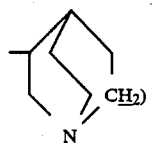

3.30 (m, 1H of

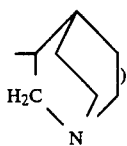

4.98 (dd, J=14 and 7.5, 1H, 5ε₁), 5.30 (m, 2H, 5α and 4α), 7.90 (dd, 1H, 1'H₆).

5δ-{[(3S)-3-Quinuclidinyl]thiomethyl]thiomethyl}pristinamycin I$_A$ may also be crystallized in the following manner:

5δ-{[(3S)-3-Quinuclidinyl]thiomethyl}pristinamycin (17.4 g) is dissolved in acetone (87 cc) which has been brought to reflux beforehand. The solution obtained is filtered and the insoluble material is rinsed with acetone (10 cc). After 3 hours at 20° C., the crystals obtained are filtered and then dried. Recrystallization of the product (14.8 g) obtained in acetone (75 cc) under the same conditions gives, after filtration followed by drying under reduced pressure (90 Pa) at 20° C., white crystals (12.2 g), m.p. about 185°–190° C.

(3S)-3-Mercaptoquinuclidine may be obtained in the following manner:

10N aqueous sodium hydroxide solution (30 cc) is added slowly to a solution of (3S)-3-(acetylthio)quinuclidine (29 g) in methanol (30 cc) maintained at approximately 25° C. The reaction mixture is stirred for 2 hours at a temperature in the region of 20° C. The pH of the reaction mixture is then brought to a value in the region of 9 by adding acetic acid (approximately 10 cc). The mixture obtained is extracted with methylene chloride (3×100 cc). The combined organic phases are dried over sodium sulphate, filtered and concentrated to dryness under reduced pressure (2.7 kPa) and 30° C. The residue obtained is purified by distillation under reduced pressure (970 Pa). (3S)-3-Mercaptoquinuclidine (12 g) is thereby obtained in the form of white crystals which melt at 46° C. and distil at 95° C. under 970 Pa ($\alpha_D^{20}$=−118°, C=1.1, methanol).

(3S)-3-(Acetylthio)quinuclidine may be obtained in a manner similar to that described in Example 1, but starting with triphenylphosphine (104.8 g), diisopropyl azodicarboxylate (80.8 g) and (3R)-3-hydroxyquinuclidine (25.7 g). (3S)-3-(Acetylthio)quinuclidine (30 g) is thereby obtained in the form of a yellow oil ]Rf=0.2; eluant: methylene chloride/methanol (90:10 by volume)]. According to R. P. Volante, Tet. Let., 22 (33), 3119 (1981) the 3 carbon of (R) configuration is converted to carbon of (S) configuration during the reaction.

(3R)-3-Hydroxyquinuclidine is prepared according to the method described by B. RINGDAHL, B. RESUL and R. DAHLBOM, Acta Pharma. Suec. 16, 281 (1979).

EXAMPLE 3

Working in a manner similar to that described in Example 1, but starting with 5δ-methylenepristinamycin I$_A$ (6.15 g) and (3R)-3-mercaptoquinuclidine (1 g), and after a purification by flash chromatography, collecting 40-cc fractions (eluant: methylene chloride/methanol (85:15 by volume)], and concentration to dryness of the fractions 20 to 30, 5δ-{[(3R)-3-quinuclidinyl]thiomethyl}pristinamycin I$_A$ (2 g) is obtained in the form of a beige powder, m.p. about 200° C.

NMR spectrum: 0.58 (dd, J=15 and 5.5, 1H, 5β₂), 1.5 to 2.2 (c,

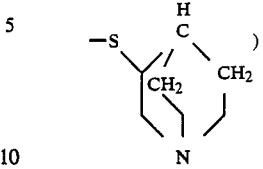

2.30 (c, 1H, 5δ), 2.35 (d, J=15, 1H, 5β₁), 2.50 (dd, 1H of —CH₂S—), 2.60 (dd, 1H, 5ε₂), 2.78 (c, 1H of

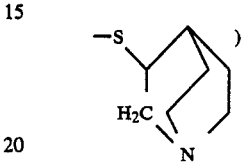

2.90 to 3.10 (c, 1H of —CH₂—S— and

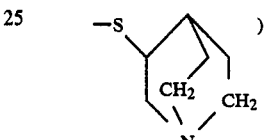

3.15 (c, 1H,

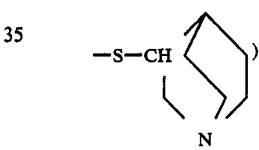

3.48 (c, 1H of

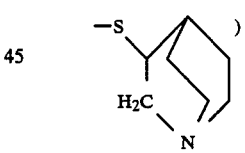

4.95 (dd, 1H, 5ε₁), 5.28 (c, 2H, 5α and 4α), 7.87 (c, 1H×0.85, 1'H₆ of the 1st isomer), 7.93 (c, 1H×0.15, 1'H₆ of the 2nd isomer), 5δ-{[(3R)-3-Quinuclidinyl]thiomethyl}pristinamycin I$_A$ may be recrystallized in the following manner:

5δ-{[(3R)-3-Quinuclidinyl]thiomethyl}pristinamycin I$_A$ (14.15 g) is dissolved in methanol (75 cc). Distilled water (4 cc) is added to this solution, which is then left to crystallize at 4° C. The crystals obtained are filtered off and then rinsed with a methanol/water (95:5 by volume) mixture (4×10 cc). After being dried under reduced pressure (90 Pa) at 42° C., white crystals (10.22 g) are obtained, m.p. about 190° C.

(3R)-3-Mercaptoquinuclidine may be obtained in a manner similar to that described in Example 2, but starting with (3R)-3-(acetylthio)quinuclidine (32.5 g) and 10N aqueous sodium hydroxide solution (35 cc); (3R)-3-mercaptoquinuclidine (11.5 g) is obtained in the form of white crystals which melt at 45° C. and distil at 90° C. under 830 Pa ($\alpha_D^{20} = +121°$, C=1.1, methanol).

(3R)-3-(Acetylthio)quinuclidine may be obtained in a manner similar to that described in Example 1, but starting with triphenylphosphine (104.8 g), diisopropyl azodicarboxylate (80.8 g) and (3S)-3-hydroxyquinuclidine (25.7 g). (3R)-3-(Acetylthio)quinuclidine (33.8 g) is thereby obtained in the form of a pale brown oil [Rf=0.4; eluant: methylene chloride/methanol (80:20 by volume)].

(3S)-3-Hydroxyquinuclidine is prepared according to the method described by B. RINGDAHL et al., Acta Pharm. Suec. 16, 281 (1979).

EXAMPLE 4

Working in a manner similar to that described in Example 1, but starting with 5δ-methylenepristinamycin $I_A$ (3.5 g) and 4-mercaptoquinuclidine (0.6 g) and after concentration to dryness, a solid is obtained which is stirred in ethyl ether. After filtration, a beige solid (3.6 g) is isolated, and purified by flash chromatography, collecting 50-cc fractions [eluant: methylene chloride/methanol (85:15 by volume)]. After concentration to dryness of fractions 19 to 35, washing with ethyl ether, filtration and then drying of the resulting solid under reduced pressure (2.7 kPa) at 20° C., 5δ-[(4-quinuclidinyl)thiomethyl]pristinamycin $I_A$ (1.2 g) is obtained in the form of an off-white powder, m.p. about 200° C.

NMR spectrum (2 isomers in respect of the 5δ carbon, in the ratio 85:15 approximately): 0.62 (dd, J=15 and 5.5, 1H, 5β₂), 1.87 (t, 6H,

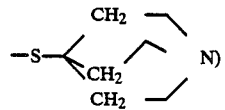

2.20 (c, 1H, 5δ), 2.28 (c, 1H, —CH₂—S—), 2.35 (d, J=15, 1H, 5β₁), 2.47 (dd, 1H, 5ε₂), 3.10 (t, 6H,

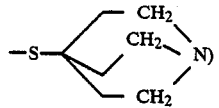

3.22 (dd, 1H, —CH₂—S—), 5.01 (dd, 1H, 5ε₁), 5.29 (broad d, J=5.5, 5α), 7.86 (c, 0.85H, 1'H₆ of the preponderant isomer), 7.92 (c, 0.15H, 1'H₆ of the minority isomer).

4-Mercaptoquinuclidine may be obtained according to the method described by A. GROB, Helv. Chim. Acta, 57, 2339 (1974).

EXAMPLE 5

The procedure is similar to that described in Example 1, but starting with 5δ-methylenevirginiamycin S (1.2 g) in methanol (20 cc) and (3R)-3-mercaptoquinuclidine (0.21 g). After purification by flash chromatography, collecting 10-cc fractions [eluant: methylene chloride/methanol (95:5 by volume) up to the fraction 35, then methylene chloride/methanol (80:20 by volume)], concentration to dryness of the fractions 47 to 55 and drying under reduced pressure (2.7 kPa) at 30° C., 5δ-{[(3R)-3-quinuclidinyl]thiomethyl}virginiamycin S (0.6 g) is obtained in the form of an off-white powder, m.p. about 185° C.

NMR spectrum (2 isomers in respect of the 5δ carbon, in the ratio 80:20 approximately): 0.4 (dd, J=15 and 5.5, 1H, 5β₂), 1.5 to 2.2 (c, 5H,

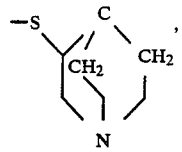

5δ), 2 (c, 1H,

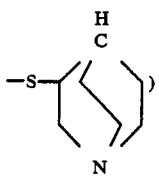

2.34 (d, J=15, 1H, 5β₁), 2.52 (dd, 1H of —CH₂S—), 2.63 (dd, 1H, 5ε₂) 2.78 (dd, 1H of

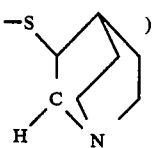

2.85 to 3.15 (c, 1H of —CH₂—S— and

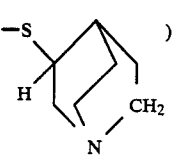

3.48 (c, 1H,

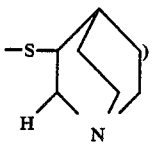

4.94 (dd, 1H, 5ε₁), 5.27 (broad d, J=5, 1H, 5α), 7.82 (dd, J=4 and 1, 1'H₆ of the 1st isomer), 7.9 (dd, J=4 and 1, 1'H₆ of the 2nd isomer).

EXAMPLE 6

The procedure is similar to that described in Example 1, but starting with 5δ-methylenevirginiamycin S (1.1 g) in methanol (20 cc) and (3S)-3-mercaptoquinuodine (0.19 g). After purification by flash chromatography, collecting 10-cc fractions [eluant: methylene chloride/methanol (90:10 by volume)], concentration to dryness of fractions 19 to 32 and drying under reduced pressure (2.7 kPa) at 30° C., 5δ-[(3S)-3-quinuclidinyl]thiomethyl-virginiamycin S (0.5 g) is obtained in the form of a pale yellow powder, m.p. about 190° C.

NMR spectrum (2 isomers in respect of the 5δ carbon, in the ratio 85:15 approximately): 0.39 (dd, J=15 and 5, 1H, 5β₂), 1.5 to 2.3 (c, 5H,

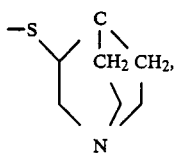

5δ), 2.11 (c, 1H,

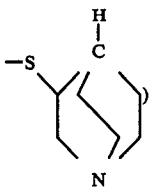

2.34 (d, J=15, 1H, 5β1), 2.52 (dd, 1H of —CH2S—), 2.64 (dd, 1H, 5ε2), 2.66 (dd, 1H of

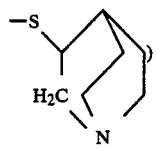

2.90 to 3.2 (c, 6H, 1H of —CH2—S—, and

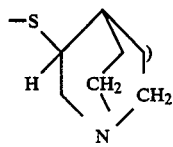

3.3 to 3.5 (c, 1H of

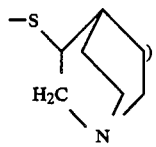

4.95 (dd, 1H, 5γ1), 5.27 (broad d, 1H, 5α), 7.80 (dd, J=4 and 1, 1H×0.85, 1'H6 of the 1st isomer), 7.90 (dd, J=4 and 1, 1H×0.15, 1'H6 of the 2nd isomer).

EXAMPLE 7

Working in a manner similar to that described in Example 2, but starting with (3S)-3-mercaptoquinuclidine (1.62 g) and stirring at −20° C. for 20 hours, a beige meringue-like product (11.4 g) is obtained after concentration to dryness under reduced pressure (2.7 kPa) at 30° C., and this is stirred in diethyl ether (100 cc), filtered and then rinsed with the same solvent (3×20 cc). This product may be recrystallized in acetone as described in Example 2, to give 5δ-{[(3S)-3-quinuclidinyl]thiomethyl}pristinamycin I$_A$ (6.6 g) in the form of white crystals, m.p. about 198°-200° C., the characteristics which are identical to those of the product obtained in Example 2, and containing 3% of minority isomer assayed by HPLC.

EXAMPLE 8

(3S)-3-Mercaptoquinuclidine (0.18 g) dissolved in acetone (5 cc) is added at −20° C. in the course of 1 hour to a solution of 5δ-methylenepristinamycin I$_A$ (1 g) in acetone (20 cc). After 18 hours' stirring at −20° C., the reaction mixture is filtered and the solid rinsed with acetone (3×2 cc). After being dried in the air, 5δ-{[(3S)-3-quinuclidinyl]thiomethyl}pristinamycin I$_A$ (0.6 g) is obtained in the form of white crystals, m.p. about 190° C., the characteristics of which are identical to those of the product obtained in Example 2 and containing 3% of the minority 5δ-isomer assayed by HPLC.

EXAMPLE 9

(3S)-3-Mercaptoquinuclidine (0.16 g) dissolved in acetone (5 cc) is added at −78° C. to a solution of 5δ-methylenepristinamycin I$_A$ (1.22 g) in acetone (15 cc), and the solution obtained is stirred under nitrogen for 24 hours at −78° C. The reaction mixture is then concentrated to dryness under reduced pressure (2.7 kPa) at 30° C. to give 1.4 g of a cream-white solid containing 5% of minority isomer assayed by HPLC and having characteristics identical to those of the product obtained in Example 2.

REFERENCE EXAMPLE 1

Trifluoroacetic acid (0.4 cc) is added at 0° C. under an atmosphere of nitrogen to 26-[(2-diisopropylaminoethyl)thio]pristinamycin II$_B$ (3.59 g) dissolved in dichloromethane (40 cc), followed by 85% pure meta-chloroperchloroperbenzoic acid (1.06 g), the temperature being maintained at 0° C. After 20 hours' stirring at 25° C., the reaction mixture is treated with saturated aqueous sodium bicarbonate solution. The organic phase is decanted and the aqueous phase then washed with methylene chloride (3×100 cc). The organic phases are combined, dried over magnesium sulphate, filtered and then concentrated to dryness under reduced pressure (2.7 kPa) at 30° C., to give a yellow solid (4.2 g) which is purified by flash chromatography [eluant: chloroform/methanol (90:10 by volume)], collecting 20-cc fractions. The fractions 22 to 28 are combined and concentrated to dryness under reduced pressure (2.7 kPa) at 30° C. to give a pale yellow solid, which is stirred in ethyl ether (10 cc). The solid obtained is separated by filtration to give 26-[(2-diisopropylaminoethyl)sulphinyl]pristinamycin II$_B$ (isomer A$_2$) (0.62 g) in the form of a yellow powder, m.p. about 155° C.

NMR spectrum: 0.90 to 1.15 [m, —CH3 at 32, 31, 30,

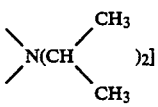

1.76 (s, —CH3 at 33), 2.75 to 3.15 (m, >CH2 at 15, —H4 and

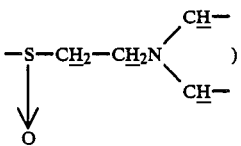

3.81 (s, >CH₂ at 17), 4.76 (d, —H₂₇), 5.51 (d, —H₁₃), 6.20 (d, —H₁₁), 6.48 (c, >NH at 8), 8.13 (s, —H₂₀).

The fractions 35 to 45 are combined and concentrated to dryness under reduced pressure (2.7 kPa) at 30° C. to give a pale yellow solid which is stirred in ethyl ether (15 cc). The solid obtained is separated by filtration to give 26-[(2-diisopropylaminoethyl)sulphinyl]pristinamycin II$_B$ (80% isomer A₁, 20% isomer A₂) in the form of a pale yellow powder, m.p. about 145° C.

NMR spectrum (isomer A₁): 1.72 (s, —CH₃ at 33), 2.70 to 3.15 (m, >CH₂ at 15, —H₄,

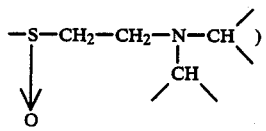

3.81 (s, >CH₂ at 17), 5.26 (d, —H₂₇), 5.46 (d, —H₁₃), 6.15 (d, —H₁₁), 8.11 (s, —H₂₀).

26-[(2-Diisopropylaminoethyl)thio]pristinamycin II$_B$ may be prepared in the following manner:

2-Diisopropylaminoethanethiol (16 g) dissolved in dichloromethane (30 cc) is added dropwise under an atmosphere of nitrogen at −30° C. to pristinamycin II$_A$ (52 g) dissolved in a mixture of dichloromethane (260 cc) and methanol (520 cc). The solution is stirred for 20 hours at −20° C. and then concentrated under reduced pressure (2.7 kPa) at 30° C. The slid obtained is stirred with ethyl ether (2×1000 cc), separated by filtration and then crystallized in acetonitrile (100 cc). The crystals are separated by filtration and then dried under reduced pressure (90 Pa) at 40° C. 26-[(2-Diisopropylaminoethyl)thio]pristinamycin II$_B$ (isomer A) (33.6 g) is thereby obtained in the form of white crystals, m.p. about 122° C.

NMR spectrum: 1 to 1.15 (m, —CH₃ isopropyl), 1.72 (s, —CH₃ at 33), 1.80 to 2.20 (m, —H₂₅, —H₂₉), 2.50 to 3 (m,

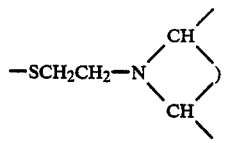

3.40 (broad d, —H₂₆), 4.74 (broad s, —H₂₇), 6.32 (m, —NH₈), 8.15 (s, —H₂₀).

2-Diisopropylaminoethanethiol may be prepared according to the method described by D. D. REYNOLDS, D. L. FIELDS and D. L. JOHNSON, J. Org. Chem. 26, 5125 (1961).

REFERENCE EXAMPLE 2

Sodium bicarbonate (1.22 g) is added to 26-[(2-diisopropylaminoethyl)thio]pristinamycin II$_B$ (isomer A) (10 g) dissolved in chloroform (300 cc). The mixture is cooled to −50° C. and 98% pure meta-chloroperbenzoic acid (2.98 g) dissolved in chloroform (100 cc) is added dropwise. The mixture is stirred for 2 hours 15 minutes at −50° C. and then treated with saturated aqueous sodium bicarbonate solution. After 15 minutes' stirring at 25° C., the mixture is decanted and the aqueous phase is then washed with dichloromethane (3×200 cc). The organic phases are combined, dried over magnesium sulphate, filtered and then concentrated to dryness under reduced pressure (2.7 kPa) at 30° C. to give a whitish meringue-like product (10.62 g). The latter is dissolved in ethyl acetate (400 cc) and then treated with 0.1N aqueous hydrochloric acid solution (140 cc). The pH of the aqueous solution is then adjusted to 4.2 by adding pH 4.2 buffer (400 cc). The aqueous phase is decanted and the organic phase washed with pH 4.2 buffer (400 cc). The aqueous phases are combined and washed with ethyl acetate (2×150 cc). After decantation, the aqueous phase is adjusted to pH 7–8 by adding sodium bicarbonate and then washed with dichloromethane (3×300 cc). The organic phases are combined and then washed with pH 7.5 buffer (2×200 cc). The aqueous phase is washed with dichloromethane (50 cc) and the organic phases are then combined, dried over magnesium sulphate, filtered and concentrated to dryness under reduced pressure (2.7 kPa) at 30° C. to give a pale yellow solid (8.04 g), which is stirred in ethyl ether (100 cc), separated by filtration and then dried under reduced pressure (90 Pa) at 40° C. 26-[(2-Diisopropylaminoethyl)sulphinyl]pristinamycin II$_B$ (isomer A₂) (7.5 g) is thereby obtained in the form of a yellow powder, m.p. about 158° C., the NMR characteristics of which are identical to those of Reference Example 1.

REFERENCE EXAMPLE 3

Working in a manner similar to that described in Reference Example 1, but starting with 26-[(2-diethylaminopropyl)thio]pristinamycin II$_B$ (6.3 g), trifluoroacetic acid (0.72 cc) and meta-chloroperbenzoic acid (1.91 g), and after purification by flash chromatography [eluant: chloroform/methanol (90:10 by volume)], collecting 60-cc fractions, and concentration to dryness of the fractions 7 to 9 under reduced pressure (2.7 kPa) at 30° C., 26-[(2-diethylaminopropyl)sulphinyl]pristinamycin II$_B$ (isomers A₂) (0.99 g) is obtained in the form of a yellow powder, m.p. about 150° C.

NMR spectrum: 1.03 to 1.20 (m, —CH₂—CH(CH₃)N(CH₂CH₃)₂ and CH₃ at 32), 1.76 (s, —CH₃ at 33), 3.82 (s, >CH₂ at 17), 4.79 (c, —H₂₇), 5.53 (d, —H₁₃), 6.20 (d, —H₁₁), 6.42 (c, >NH at 8), 8.13 (s, —H₂₀).

After concentration to dryness of the fractions 23 to 35 under reduced pressure (2.7 kPa) at 30° C., 26-[(2-diethylaminopropyl)sulphinyl]pristinamycin II$_B$ (isomers A₁) (0.64 g) is obtained in the form of a beige-yellow powder, mp about 160°–170° C.

NMR spectrum: 1.14 (m, —N(CH₂CH₃)₂), 1.24 (broad d,

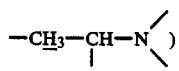

1.73 (s, —CH₃ at 33), 3.81 (limiting AB, >CH₂ at 17), 5.28 (d, —H₂₇), 5.43 (d, —H₁₃), 6.15 (d, —H₁₁), 6.88 (c, >NH at 8), 8.10 (s, —H₂₀).

26-[(2-Diethylaminopropyl)thio]pristinamycin II$_B$ may be prepared in the following manner:

Working in a manner similar to that described in Example 1 of European patent application EP No. 135,410, but starting with pristinamycin II$_A$ (3.15 g) and 2-diethylaminopropanethiol (1.8 g), and after purification by flash chromatography [eluant: methylene chloride/methanol (90:10 by volume)], collecting 20-cc fractions, and concentration to dryness of the fractions 3 to 5 under reduced pressure (2.7 kPa) at 30° C., 26-[(2-diethylaminopropyl)thio]pristinamycin II$_B$ (1.4 g) is obtained in the form of a yellow powder, m.p. about 160° C.

NMR spectrum: 1 (c, 9H: —H$_{32}$+—N(CH$_2$CH$_3$)$_2$), 2.50 (c, 6H:

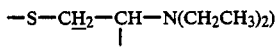

3.30 (c, 1H: —H$_{26}$), 4.70 (d, 1H: —H$_{27}$), 8.12 (s, 1H: —H$_{20}$).

2-Diethylaminopropanethiol may be prepared in the following manner:

10N aqueous sodium hydroxide solution (25 cc) is added to a soluton of 1-(S-isothioureido)-2-diethylaminopropane dihydrochloride (29.5 g) in distilled water (150 cc). The mixture is brought to 100° C. for 1 hour, cooled to 20° C., adjusted to pH 9 by adding 12N aqueous hydrochloric acid solution (8 cc) and then extacted with ethyl ether (3×100 cc). The ether phases are combined, dried over potassium carbonate, filtered and then concentrated to dryness under reduced pressure (2.7 kPa) at 30° C. The mixture is purified by distillation. 2-Diethylamino-1-propanethiol (5.8 g) is obtained in the form of a colourless liquid [b.p. (2.7 kPa) 78° C.].

1-(S-Isothioureido)-2-diethylaminopropane dihydrochloride may be prepared in the following manner:

Thiourea (16.7 g) is added to a solution of 1-chloro-2-diethylaminopropane hydrochloride (41 g) in dimethylformamide (200 cc). The mixture is brought to 100° C. for 30 minutes, and then cooled to 20° C. The white precipitate formed is collected by filtration, and washed with dimethylformamide (3×20 cc) and then ethyl ether (3×20 cc). 1-(S-Isothioureido)-2-diethylaminopropane dihydrochloride (29.6 g) is obtained in the form of white crystals, m.p. 247°–249° C.

1-Chloro-2-diethylaminopropane hydrochloride may be obtained in the following manner:

2-Diethylaminopropanol hydrochloride (45.2 g) is added in the course of 15 minutes to thionyl chloride (100 cc), and the mixture is then heated to 80° C. After 2 hours' stirring, the excess thionyl chloride is distilled off and the residue taken up with ethyl ether (200 cc). 1-Chloro-2-diethylaminopropane hydrochloride crystallizes. After filtration, white crystals (48.2 g) are obtained, m.p. 112° C.

2-Diethylaminopropanol hydrochloride may be obtained in the following manner:

A solution of ethyl 2-diethylaminopropionate (66 g) in ethyl ether (330 cc) is added slowly at 20° C. to a suspension, maintained under nitrogen, of lithium aluminium hydride (10.6 g) in ethyl ether (1 liter). The reaction is maintained at a temperature of 35° C. for 5 hours, and the temperature is then lowered to 0° C. Water (12.4 cc), 5N aqueous sodium hydroxide solution (9.1 cc) and then water (41.3 cc) are then added dropwise at 0° C., the mixture is stirred for 30 minutes, then filtered on sintered glass and then washed with ethyl ether. The ether phase is dried over potassium carbonate, filtered and then concentrated to dryness under reduced pressure (2.7 kPa) at 30° C. A yellow liquid (43.8 g) is obtained, which is dissolved in acetone (200 cc), and a 4.5N solution (78 cc) of hydrogen chloride gas in ethyl ether is then added. 2-Diethylaminopropanol hydrochloride crystallizes. After filtration, white crystals (45.2 g) are obtained, m.p. 97°–100° C.

Ethyl 2-diethylaminopropionate may be obtained according to BRAUN et al., Beilstein, 61, 1425 (1928).

REFERENCE EXAMPLE 4

The procedure is similar to that described in Reference Example 2, but starting with 26-[(2-diethylaminopropyl)thio]pristinamycin II$_B$ (isomers A) (4 g), 98% pure meta-chloroperbenzoic acid (1.16 g) and solid sodium bicarbonate (1 g). After purification by flash chromatography [eluant: chloroform/methanol (93:7 by volume)] and concentration to dryness of the fractions 21 to 48 under reduced pressure (2.7 kPa) at 30° C., collecting 25-cc fractions, 26-[(2-diethylaminopropyl)sulphinyl]pristinamycin II$_B$ (isomers A$_2$) (2.69 g) is obtained in the form of a yellow powder having characteristics identical to those of the product obtained in Reference Example 3.

26-[(2-Diethylaminopropyl)thio]pristinamycin II$_B$ (isomer A) may be obtained by working in a manner similar to that described in Reference Example 1, but starting with pristinamycin II$_A$ (15 g) and 2-diethylaminopropanethiol (4.62 g). After purification by flash chromatography (eluant: chloroform/methanol (90:10 by volume)] and concentration to dryness of the fractions 27 to 52 under reduced pressure (2.7 kPa) at 30° C., collecting 40-cc fractions, a yellow solid (12 g) is obtained, which is stirred in ethyl ether (60 cc), filtered and then dried. 26-[(2-Diethylaminopropyl)thio]pristinamycin II$_B$ (isomer A) (8.2 g) is obtained in the form of a pale yellow powder, m.p. about 122° C.

NMR spectrum:
1 to 1.15 (m, ethyl-CH$_3$ + C$\underline{H}_3$—CH—N(C$_2$H$_5$)$_2$)
1.70 (s, —CH$_3$ at 33)

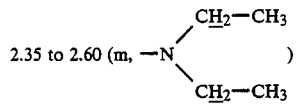

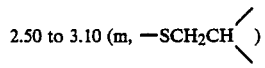

2.75 (m, —H$_4$)

2.89 and 3.05 (2dd  
2.92 and 3.08 (2dd  } ＼CH$_2$ at 15) ／

3.30 (m  
3.37 (m } —H$_{26}$)

3.80 (s, ＼CH$_2$ at 17) ／

4.69 (d  
4.71 (d } —H$_{27}$)

5.45 (d, —H$_{13}$)

-continued 6.13 (d)
6.14 (d) } —H$_{11}$)

6.4 to 6.60 (m, \NH at 8)
            /

6.51 (dd)
6.53 (dd) } —H$_5$)

8.09 (s, —H$_{20}$)

REFERENCE EXAMPLE 5

The procedure is similar to that described in Reference Example 2, but starting with 26-[(1-diethylamino-2-propyl)thio]pristinamycin II$_B$ (isomers A) (4.58 g), 98% pure meta-chloroperbenzoic acid (1.29 g) and solid sodium bicarbonate (1.14 g). After purification by flash chromatography [eluant: chloroform/methanol (97:3 by volume)], collecting 20-cc fractions, and concentration to dryness under reduced pressure (2.7 kPa) at 30° C., of the fractions 59 to 77 and the fractions 79 to 97, respectively, the following are obtained: from the fractions 79 to 97, 26-[(1-diethylamino-2-propyl)sulphinyl]-pristinamycin II$_B$ (1st isomer) (1.47 g) in the form of a pale yellow solid, m.p. about 132° C.;

NMR spectrum: 1.02 (t, ethyl—CH$_3$), 1.34 (d,

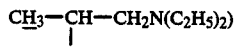
CH$_3$—CH—CH$_2$N(C$_2$H$_5$)$_2$
      |

1.72 (s, —CH$_3$ at 33), 2.5 to 2.7 (m,

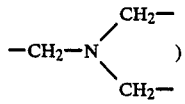
         /CH$_2$—
—CH$_2$—N       )
         \CH$_2$—

2.77 (m, —H$_4$), 2.87 and 3.09 (2dd, >CH$_2$ at 15), 2.97 (m,

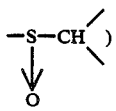
       /
—S—CH    )
       \
   ↓
   O 3.72 (m, —H$_{26}$), 3.80 (s, >CH at 17), 4.92 (m, —H$_{27}$), 5.43 (d, —H$_{13}$), 6.15 (d, —H$_{11}$), 6.72 (dd, >NH at 8), 8.06 (s, —H$_{20}$).
and from the fractions 59 to 77, 26-[(1-diethylamino-2-propyl)sulphinyl]pristinamycin II$_B$ (second isomer) (1.07 g) in the form of a pale yellow solid, m.p. 128° C.;

NMR spectrum: 1.72 (s, CH$_3$ at 33), 3.4 (m, —H$_{26}$), 3.79 (s, CH$_2$ at 17), 4.74 (m, —H$_{27}$), 5.48 (d, —H$_{13}$), 6.18 (d, —H$_{11}$), 6.80 (m, >NH at 8), 8.09 (s, —H$_{20}$).

26-[(1-Diethylamino-2-propyl)thio]pristinamycin II$_B$ (isomers A) may be obtained by working in a manner similar to that described in Example 1, but starting with pristinamycin II$_A$ (13 g) and 1-diethylamino-2-propanethiol (4 g). After purification by flash chromatography [eluant: chloroform/methanol (90:10 by volume)] and concentration to dryness of the fractions 46 to 55 under reduced pressure (2.7 kPa) at 30° C., collecting 50-cc fractions, a pale yellow solid (8 g) is obtained, which is crystallized in acetonitrile (30 cc). After filtration and drying, 26-[(1-diethylamino-2-propyl)thio]pristinamycin II$_B$ (isomers A) (5.91 g) is obtained in the form of white crystals, m.p. 136° C.

NMR spectrum: 0.9 to 1.10 (m, —N(CH$_2$CH$_3$)$_2$) 1.33 to 1.37 (2d,

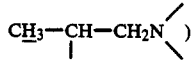
CH$_3$—CH—CH$_2$N/
      |        \

1.7 (s, —CH$_3$ at 33), 2.4 to 2.65 (m,

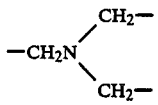
          /CH$_2$—
—CH$_2$N
          \CH$_2$—

2.76 (m, —H$_4$), 3 (m, —S—CH<), 2.9 to 3.1 (2dd, >CH$_2$ at 15), 3.52 (m, —H$_{26}$), 3.81 (s, >CH$_2$ at 17), 4.78 (m, —H$_{27}$), 5.46 (d, —H$_{13}$), 6.14 (d, —H$_{11}$), 6.40 (m, >NH at 8), 8.09 and 8.10 (2s, —H$_{20}$).

1-Diethylamino-2-propanethiol may be obtained according to the method described by R. T. WRAGG, J. Chem. Soc. (C), 2087 (1969).

REFERENCE EXAMPLE 6

The procedure is similar to that described in Reference Example 2, but starting with 26-{[(2R)-2-dimethylaminobutyl]thio}pristinamycin II$_B$ (isomer A) (1.7 g), sodium bicarbonate (0.50 g) and 98% pure meta-chloroperbenzoic acid (0.45 g). After purification by flash chromatography (eluant: ethyl acetate/methanol (85:15 by volume)] and concentration to dryness of the fractions 35 to 58 under reduced pressure (2.7 kPa) at 30° C., a white solid (1.1 g) is obtained, which is stirred in ethyl ether (30 cc). After filtration and drying, 26-{[(2R)-2-dimethylaminobutyl]sulphinyl}pristinamycin II$_B$ (isomer A$_2$) (0.95 g) is obtained in the form of a white solid, m.p. about 126° C.

NMR spectrum: 1 (m,

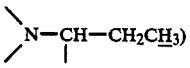
\
 >N—CH—CH$_2$CH$_3$
/     |

1.45 to 1.75 (m,

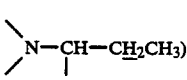
\
 >N—CH—CH$_2$CH$_3$
/     |

1.78 (s, —CH$_3$ at 33), 2.50 to 3.05 (m,

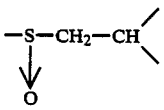
           /
—S—CH$_2$—CH
           \
   ↓
   O and —H$_4$), 2.93 and 3.14 (2dd, >CH$_2$ at 15), 3,31 (m, —H$_{26}$), 3.84 (s, >CH$_2$ at 17), 4.84 (d, —H$_{27}$), 5.51 (d, —H$_{13}$), 6.19 (d, —H$_{11}$), 6.30 (dd, >NH at 8), 8.15 (s, —H$_{20}$).

26-{[(2R)-2-Dimethylaminobutyl]thio}pristinamycin II$_B$ (isomer A) may be obtained by working in a manner similar to that described in Reference Example 1, but starting with pristinamycin II$_A$ (8 g) and (2R)-2-dimethylaminobutanethiol (2.3 g). After purification by flash chromatography [eluant: dichloromethane/methanol (90:10 by volume)] and concentration to dryness of the fractions 36 to 55 under reduced pressure (2.7 kPa) at 30° C., 26-{[(2R)-2-dimethylaminobutyl]thio}pristinamycin II$_b$ (isomer A) (3 g) is obtained in the form of a pale yellow solid, m.p. about 120° C.

Crystallization of 0.9 g of this product in acetonitrile (5 cc) leads, after separation by filtration, to 26-{[(2R)-2-dimethylaminobutyl]thio}pristinamycin II$_B$ (isomer A) (0.2 g) in the form of white crystals, m.p. 122° C.

NMR spectrum: 1 (m,

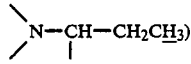

1.4 to 1.7 (m,

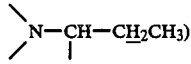

1.72 (s, —CH$_3$ at 33), 2.30 (s, —N(CH$_3$)$_2$), 2.5 to 2.85 (m, —S—CH$_2$—CH< and —H$_4$), 2.93 and 3.10 (2dd, >CH$_2$ at 15), 3.34 (broad d, —H$_{26}$), 3.83 (s, >CH$_2$ at 17), 4.76 (broad s, —H$_{27}$), 5.48 (d, —H$_{13}$), 6.14 (d, —H$_{11}$), 6.26 (dd, >NH at 8), 8.13 (s, —H$_{20}$).

(R)-2-Dimethylaminobutanethiol may be obtained in a manner similar to that described below in Reference Example 7, starting with triphenylphosphine (52.4 g), diisopropyl azodicarboxylate (40 cc), (R)-2-dimethylaminobutanol (12 g) and thiolacetic acid (15.2 cc) (in this case, the intermediate thioester is hydrolysed directly during the chromatography on silica gel.

After purification by flash chromatography [eluant: dichloromethane (1000 cc), then dichloromethane/methanol (85:15 by volume; 2000 cc), then dichloromethane/methanol (80:20 by volume; 4000 cc)], collecting 100-cc fractions, and concentration to dryness of fractions 42 to 60 under reduced pressure, a yellow oil (14 g) is obtained, which is purified by distillation. (R)-2-Dimethylaminobutanethiol (2.4 g) is thereby obtained in the form of a colourless liquid [b.p. (4 kPa) 70°-75° C.].

(R)-2-Dimethylamino-1-butanol may be obtained in a manner identical to that described by M. WENGHOEFER et al., J. Heterocycl. Chem., 7(6), 1407 (1970).

REFERENCE EXAMPLE 7

Working in a manner similar to that described in Reference Example 2, but starting with 26-{[(2S)-2-dimethylamino-3-phenylpropyl]thio}pristinamycin II$_B$ (isomer A) (2.67 g), sodium bicarbonate (0.7 g) and 98% pure metachloroperbenzoic acid (0.7 g), after purification by flash chromatography [eluant: chloroform/methanol (90:10 by volume)], collecting 20-cc fractions, and concentration to dryness of the fractions 19 to 23 under reduced pressure (2.7 kPa) at 30° C., a pale yellow solid (1.3 g) is obtained, which is stirred in ethyl ether (50 cc) and separated by filtration to give 26-{[(2S)-2-dimethylamino-3-phenylpropyl]sulphinyl}pristinamycin II$_B$ (isomer A$_2$) (1.18 g) in the form of a pale yellow solid, m.p. about 150° C.

NMR spectrum (400 MHz, CDCl$_3$)
1.73 (s, —CH$_3$ at 33)

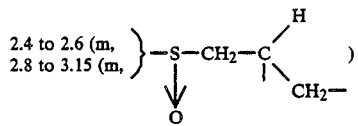

2.44 (s, —N(CH$_3$)$_2$)
2.77 (m, —H$_4$)

2.89 and 3.1 (2dd, >CH$_2$ at 15)

3.18 (m, —H$_{26}$)

3.82 (s, >CH$_2$ at 17)

4.68 (d, —H$_{27}$)
5.51 (d, —H$_{13}$)
6.19 (d, —H$_{11}$)

6.50 (dd, >NH at 8)

7.18 (d, ortho-H of the phenyl)
7.23 (t, para-H of the phenyl)
7.31 (t, meta-H of the phenyl)
8.13 (s, —H$_{20}$)

A 1% strength aqueous solution of 26-{[(2S)-2-dimethylamino-3-phenylpropyl]sulphinyl}pristinamycin II$_B$ (isomer A$_2$) is obtained with the following:
product: 30 mg
0.1N hydrochloric acid: 0.45 cc
distilled water: qs 3 cc 26-{[(2S)-2-Dimethylamino-3-phenylpropyl]thio}pristinamycin{II$_B$ (isomer A) may be prepared by working in a manner similar to that described in Example 1 for the preparation of the starting substance, but starting with pristinamycin II$_A$ (7.13 g) and (S)-2-dimethylamino-3-phenylpropanethiol (2.65 g) and, after purification by flash chromatography [eluant: ethyl acetate/methanol (80:20 by volume)], collecting 60-cc fractions, and concentration to dryness of the fractions 33 to 43 under reduced pressure (2.7 kPa) at 30° C., a pale yellow solid (4.6 g) is obtained, which is stirred in ethyl ether (50 cc), filtered and then dried under reduced pressure (90 Pa) at 45° C. 26-{[(2S)-2-Dimethylamino-3-phenylpropyl]thio}pristinamycin II$_B$ (isomer A) (3.6 g) is thereby obtained in the form of a pale yellow powder, m.p. about 110° C.

NMR spectrum: 1.69 (s, —CH$_3$ at 33), 2.38 (s, —N(CH$_3$)$_2$), 2.35 to 3.05 (m,

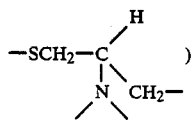

2.73 (m, —H$_4$), 2.89 to 3.10 (2dd, >CH$_2$ at 15), 3.26 (broad d, —H$_{26}$), 3.81 (s, >CH$_2$ at 17), 4.68 (broad s, —H$_{27}$), 5.47 (d, —H$_{13}$), 6.12 (d, —H$_{11}$), 6.27 (m, >NH at 8), 7.18 (d, ortho-H of the phenyl), 7.21 (t, para-H of the phenyl), 7.30 (t, meta-H of the phenyl), 8.11 (s, —H$_{20}$).

(S)-2-Dimethylamino-3-phenylpropanethiol may be prepared in the following manner:

Sodium methylate (0.2 g) is added under an atmosphere of nitrogen to (S)-2-dimethylamino-3-phenylpropanethiol acetate (crude; 20 g) dissolved in methanol (50 cc), and the mixture is heated under reflux for 2 hours. The mixture is then concentrated to dryness under reduced pressure (2.7 kPa) at 30° C. to give a liquid which is purified by distillation. (S)-2-Dimethylamino-3-phenylpropanethiol (2.4 g) is obtained in the form of a colourless liquid [b.p. (14 Pa)=95° C.], which is used as it is in the following reaction.

(S)-2-Dimethylamino-3-phenylpropanethiol acetate may be prepared in the following manner:

Triphenylphosphine (41.97 g) and tetrahydrofuran (310 cc) are added to 0° C. under an atmosphere of nitrogen, diisopropyl azodicarboxylate (31.5 cc) is then added dropwise and the mixture is left with stirring for half an hour at 0° C. A mixture of (S)-2-dimethylamino-3-phenylpropanol (15 g) and thiolacetic acid (11.44 cc) dissolved in tetrahydrofuran (160 cc) is added dropwise to the white suspension obtained. After 1 hour's stirring at 0° C. followed by 1 hour 30 minutes at 25° C., the mixture is concentrated to dryness under reduced pressure (2.7 kPa) at 30° C. The oil obtained is treated with methanol (190 cc), the white solid which precipitates is removed by filtration and the filtrate is concentrated to dryness under reduced pressure (2.7 kPa) at 30° C. The residue is then stirred with isopropyl ether (200 cc), the white solid precipitate is again removed by filtration and the filtrate is concentrated to give a yellow oil (45 g) which is purified by flash chromatography [eluant: dichloromethane/methanol (90:10 by volume)], collecting 100-cc fractions. After concentration to dryness of the fractions 37 to 55 under reduced pressure (2.7 kPa) at 30° C., (S)-2-dimethylamino-3-phenylpropanethiol acetate (10.4 g) is obtained in the form of an orange-yellow oil (containing triphenylphosphine oxide).

(S)-2-Dimethylamino-3-phenylpropanol may be prepared by analogy with the method described by T. HAYASHI et al., J. Org. Chem., 48, 2195 (1983).

REFERENCE EXAMPLES 8 TO 26

Working in a manner similar to that described in Reference Example 2, the following products are prepared:

| Reference Example | R | n | (1) Isomer (2) Melting point |
|---|---|---|---|
| 8 | —(CH$_2$)$_2$N(C$_2$H$_5$)$_2$ | 1 | (1) isomer A<br>(2) M.p. ~172° C. |
| 9 | —(CH$_2$)$_2$N(CH$_3$)$_2$ | 1 | (1) isomer A$_2$ 70%<br>isomer A$_1$ 15%<br>isomer B$_1$ 7%<br>isomer B$_2$ 8%<br>(2) M.p. ~150° C. |
| 10 | —(CH$_2$)N—C$_2$H$_5$<br>    \|<br>   CH$_3$ | 1 | (1) isomer A$_2$<br>(2) M.p. ~145° C. |
| 11 | —(CH$_2$)$_3$N(CH$_3$)$_2$ | 1 | (1) isomer A$_2$ 45%<br>isomer B$_2$ 35%<br>isomer B$_1$ 15%<br>(2) M.p. ~165° C. |
| 12 | —(CH$_2$)$_2$—N(azetidinyl) | 1 | (1) isomer A$_1$ 60%<br>isomer A$_2$ 25%<br>isomer B$_1$ 15%<br>(2) M.p. ~175° C. |
| 13 | —(CH$_2$)$_2$—N(pyrrolidinyl) | 1 | (1) isomer A$_2$ 75%<br>isomer A$_1$ 5%<br>isomer B$_1$ 10%<br>isomer B$_2$ 10%<br>(2) M.p. ~145° C. |
| 14 | —(CH$_2$)$_2$—N(piperidinyl) | 1 | (1) isomer A$_2$ 90%<br>isomer A$_1$ 10%<br>(2) M.p. ~162° C. |
| 15 | —(CH$_2$)$_2$—N(piperidinyl) | 1 | (1) isomer A$_1$ 50%<br>isomer A$_2$ 50%<br>(2) M.p. ~152° C. |

-continued

| Reference Example | R | n | (1) Isomer (2) Melting point |
|---|---|---|---|
| 16 | —(CH₂)₂—N(=N ring, pyrazole-like) | 1 | (1) isomer A₂ (2) M.p. ~170° C. |
| 17 | —(CH₂)₂—N(morpholine, O) | 1 | (1) isomer A₂ (2) M.p. ~126° C. |
| 18 | —(CH₂)₂NHC₄H₉ | 1 | (1) isomer A₂ 70% isomer B₁ 15% isomer B₂ 15% (2) M.p. ~140° C. |
| 19 | —(CH₂)₂NHC₄H₉ | 1 | (1) isomer A₁ 85% isomer B₁ 15% (2) M.p. ~170° C. |
| 20 | —(CH₂)₂NHC₄H₉ | 1 | (1) isomer B₁ 65% isomer B₂ 35% (2) M.p. ~140° C. |
| 21 | —(CH₂)₂NHC₁₀H₂₁ | 1 | (1) isomer A₂ 80% (2) M.p. ~128° C. |
| 22 | —(CH₂)₂NHC₁₀H₂₁ | 1 | (1) isomer A₂ 50% isomer A₁ 15% isomer B₁ 20% isomer B₂ 15% (2) M.p. ~124° C. |
| 23 | —(CH₂)₂—NH—(cyclohexyl) | 1 | (1) isomer A₂ 90% (2) M.p. ~166° C. |
| 24 | —(CH₂)₂—N(CH₃)—(cyclohexyl) | 1 | (1) isomer A₂ (2) M.p. ~126° C. |
| 25 | —(CH₂)₂OCON(piperazine)N—CH₃ | 1 | (1) isomer A₂ (2) M.p. ~135° C. |
| 26 | —(CH₂)₂OCON(piperazine)N—CH₃ | 1 | (1) isomer A₁ (2) M.p. ~140° C. |

REFERENCE EXAMPLE 27

Working in the manner similar to that described in Reference Example 1, but starting with 26-{[(S)-1-methyl-2-pyrrolidinyl]methylthio}pristinamycin II$_B$ (isomer A) (7.8 g), trifluoroacetic acid (0.91 cc) and meta-chloroperbenzoic acid (2.4 g) and after purification by flash chromatography [eluant: chloroform/methanol (90:10 by volume)], collecting 60-cc fractions, and concentration to dryness of the fractions 26 to 36 under reduced pressure (2.7 kPa) at 30° C., 26-{[(S)-1-methyl-2-pyrrolidinyl]methylsulphinyl}pristinamycin II$_B$ (isomer A₂ (2.3 g) is obtained in the form of a pale yellow powder, m.p. about 140° C.

NMR spectrum: 1.76 (s, —CH₃ at 33), 2.48 (s, >NCH₃), 1.70 to 2.60 (m, —H₂₉ and >CH₂ at 25 and 50 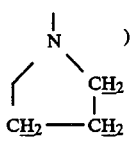 2.75 to 3.25 (m,

—S—CH₂—CH(>)
↓
O
), 3.82 (s, >CH₂ at 17), 4.81 (d, —H₂₇), 5.52 (d, —H₁₃), 6.20 (d, —H₁₁), 6.42 (dd, >NH at 8), 8.14 (s, —H₂₀).

After concentration to dryness of the fractions 46 to 59 under reduced pressure (2.7 kPa) at 30° C., 26-{[(S)-

1-methyl-2-pyrrolidinyl]methylsulphinyl}pristinamycin II$_B$ (isomer A$_1$) (1.1 g) is obtained in the form of a pale yellow powder, m.p. about 148° C.

NMR spectrum: 1.73 (s, —CH$_3$ at 33), 1.70 to 2.50 (m,

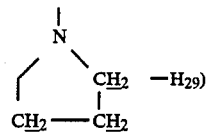

2.41 (s, >N—CH$_3$), 2.65 to 3.25 (m, >CH$_2$ at 15, —H to 4,

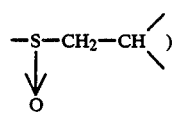

3.82 (limiting AB, >CH$_2$ at 17), 5.45 (d, —H$_{13}$), 6.17 (d, —H$_{11}$), 8.11 (s, —H$_{20}$).

26-[(1-Methyl-2-pyrrolidinyl)methylthio]pristinamycin II$_B$ may be prepared in the following manner:

Working in a manner similar to that described in Example 1 of U.S. Pat. No. 4,590,004, but starting with pristinamycin II$_A$ (10.5 g) and [(S)-1-methyl-2-pyrrolidinyl]methanethiol (3.14 g) and after purification by flash chromatography [eluant: chloroform/methanol (90:10 by volume)] and concentration to dryness of the fractions 20 to 35 under reduced pressure (2.7 kPa) at 30° C., the A isomer (7.8 g) is obtained in the form of a yellow powder, m.p. approximately 120° C.

NMR spectrum: 1.70 (s, —CH$_3$ at 33), 2.38 (s, >N—CH$_3$), 1.70 to 2.50 (m, —H$_{29}$, CH$_2$ at 25 and

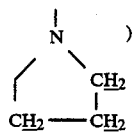

2.6 to 3.20 (m, —S—CH$_2$—CH<), 3.82 (s, >CH$_2$ at 17), 4.73 (d, —H$_{27}$), 5.45 (d, —H$_{13}$), 6.15 (d, —H$_{11}$), 6.41 (dd, >NH at 8), 8.11 (s, —H$_{20}$).

4N aqueous sodium hydroxide solution (100 cc) is added to crude S-[(S)-1-methyl-2-pyrrolidinylmethyl]isothiouronium dihydrochloride (25 g) dissolved in distilled water (100 cc), and the mixture is then stirred at 90° C. under an atmosphere of nitrogen for 2 hours. The reaction mixture is cooled to 0° C., treated with 12N aqueous hydrochloric acid solution (25 cc) and then extracted with methylene chloride (2×200 cc). The organic phase is dried over sodium sulphate, filtered and then concentrated to dryness under reduced pressure (2.7 kPa) at 30° C. [(S)-1-Methyl-2-pyrrolidinyl]methanethiol (5.9 g) is thereby obtained in the form of a pale yellow oil, which is used in the next stage of the reaction without further purification.

Rf=0.15; silica gel chromatography; eluant: chloroform/methanol (90:10 by volume).

Thiourea (10.7 g) is added to [(S)-1-methyl-2-pyrrolidinyl]chloromethane hydrochloride (11.9 g) dissolved in ethanol (50 cc), and the mixture is then stirred under reflux for 48 hours. The mixture is concentrated to dryness under reduced pressure (2.7 kPa) at 40° C. The residue is taken up with hot ethanol (100 cc) and then filtered on activated vegetable charcoal. After concentration to dryness of the filtrate under reduced pressure (2.7 kPa) at 40° C., a pale yellow oil (25 g) is obtained, composed of S-[(S)-1-methyl-2-pyrrolidinylmethyl]isothiouronium dihydrochloride and excess thiourea.

Rf=0.1; silica gel chromatoplate; eluant: chloroform/methanol (90:10 by volume).

[(S)-1-Methyl-2-pyrrolidinyl]chloromethane hydrochloride may be prepared according to the method described by T. HAYASHI et al., J. Org. Chem., 48, 2195 (1983).

REFERENCE EXAMPLE 28

Working in a manner similar to that described in Reference Example 1, but starting with 26-[(1-methyl-4-piperidyl)thio]pristinamycin II$_B$ (2.6 g), trifluoroacetic acid (0.3 cc) and meta-chloroperbenzoic acid (0.8 g) and after purification by flash chromatography [eluant: chloroform/methanol (90:10 by volume)], collecting 40-cc fractions, and concentration to dryness of the fractions 20 to 35 under reduced pressure (2.7 kPa) at 30° C., 26-[(1-methyl-4-piperidyl)sulphinyl]pristinamycin II$_B$ (isomer A$_2$) (0.33 g) is obtained in the form of a yellow powder, m.p. about 170° C.

NMR spectrum: 1.76 (s, —CH$_3$ at 33), 2.2 to 3.00 (m,

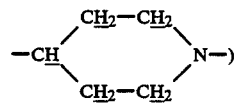

2.32 (s, >N—CH$_3$), 3.82 (s, CH$_2$ at 17), 4.85 (d, —H$_{27}$), 5.50 (d, —H$_{13}$), 6.19 (d, —H$_{11}$), 6.37 (dd, >NH at 8), 8.15 (s, —H$_{20}$).

26-[(1-Methyl-4-piperidyl)thio]pristinamycin II$_B$ may be obtained in the following manner:

Working in a manner similar to that described in Example 1 of U.S. Pat. No. 4,590,004, but starting with pristinamycin II$_A$ (3.15 g) and 1-methyl-4-piperidinethiol (1.6 g) with the addition of triethylamine (0.6 g) to the reaction mixture and, after purification by flash chromatography [eluant: methylene chloride/methanol (92:8 by volume)] and concentration to dryness of the fractions 4 to 20 under reduced pressure (2.7 kPa) at 30° C., 26-[(1-methyl-4-piperidyl)thio]pristinamycin II$_B$ (0.9 g) is obtained in the form of a yellow powder, m.p. about 180° C.

NMR spectrum: 2.10 (c, 4H:

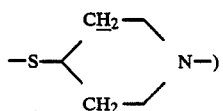

2.25 (s, 3H:

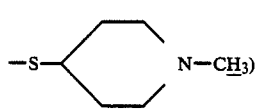

2.80 (c, 4H:

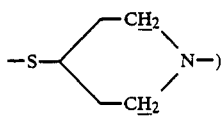

3.55 (c, 1H: —H$_{26}$), 4.26 (c, 1H: —H$_{27}$), 7.70 (c, 1H: —H$_8$), 8.10 (s, 1H: —H$_{20}$).

1-Methyl-4-piperidinethiol may be prepared by the method described by H. BARRER and R. E. LYLE, J. Org. Chem., 27, 641 (1962).

REFERENCE EXAMPLE 29

Trifluoroacetic acid (0.92 cc) is added at 0° C. under an atmosphere of nitrogen to 26-[(2-diethylaminoethyl)-thio]pristinamycin II$_B$ (7.8 g) dissolved in methanol (60 cc). After 15 minutes at 0° C., the temperature is raised to 15° C. and selenium dioxide (1.37 g) is then added. When all the selenium dioxide is dissolved, 30% strength aqueous hydrogen peroxide solution (7 cc) is added slowly at a temperature below 25° C. After 1 hour's stirring at 25° C., the reaction mixture is cooled to 10° C., treated with saturated aqueous sodium bicarbonate solution (50 cc) and then extracted with methylene chloride (4×50 cc). The organic phases are combined, dried over magnesium sulphate, filtered and then concentrated to dryness under reduced pressure (2.7 kPa) at 30° C. The yellow solid obtained is purified by flash chromatography [eluant: chloroform/methanol (90:10 by volume)], collecting 40-cc fractions. After concentration to dryness of the fractions 31 to 38 under reduced pressure (2.7 kPa) at 30° C., a yellow solid is obtained which is purified by flash chromatography [eluant: ethyl acetate/methanol (80:20 by volume)], collecting 40-cc fractions. After concentration to dryness of the fractions 27 to 33 under reduced pressure, a white solid is obtained which is stirred in ethyl ether (50 cc), separated by filtration and then dried under reduced pressure (90 Pa) at 30° C. 26-[(2-Diethylaminoethyl)sulphonyl]pristinamycin II$_B$ (isomer A) (0.5 g) is thereby obtained in the form of a white solid, m.p. about 150° C.

NMR spectrum: 0.97 (d, —CH$_3$ at 30 and —CH$_3$ of the ethyl), 1.75 (s, —CH$_3$ at 33), 2.62 (q,

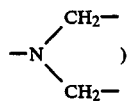

3.00 to 3.40 (m, —SO$_2$CH$_2$CH$_2$N<), 3.82 (s, >CH$_2$ at 17), 5.34 (d, —H$_{13}$), 5.43 (d, —H$_{13}$), 6.16 (d, —H$_{11}$), 6.54 (dd, >NH at 8), 8.10 (s, —H$_{20}$).

REFERENCE EXAMPLE 30

The procedure is similar to that described in Reference Example 29, but starting with 26-[(2-diisopropylaminoethyl)thio]pristinamycin II$_B$ (isomer A) (6.86 g), trifluoroacetic acid (0.77 cc), selenium dioxide (1.15 g) and 30% strength aqueous hydrogen peroxide solution (6.33 cc). After purification by flash chromatography [eluant: ethyl acetate/methanol (80:20 by volume)] collecting 40-cc fractions, and concentration to dryness of the fractions 28 to 31 under reduced pressure (2.7 kPa) at 30° C., a yellow solid (0.7 g) is obtained, which is purified again by flash chromatography [eluant: ethyl acetate/methanol (85:15 by volume)], collecting 30-cc fractions. After concentration to dryness of the fractions 26 to 33 under reduced pressure, a yellow solid is obtained which is stirred in ethyl ether (30 cc), separated by filtration and then dried under reduced pressure (90 Pa) at 30° C. 26-[(2-Diisopropylaminoethyl)sulphonyl]pristinamycin II$_B$ (isomer A) (0.6 g) is obtained in the form of a pale yellow solid, m.p. about 140° C.

NMR spectrum: 1.06 (d, —CH$_3$ isopropyl), 1.75 (s, —CH$_3$ at 33), 2.79 (m, —H$_4$), 2.92 and 3.10 (2dd, >CH$_2$ at 15), 2.7 to 3.30 (m,

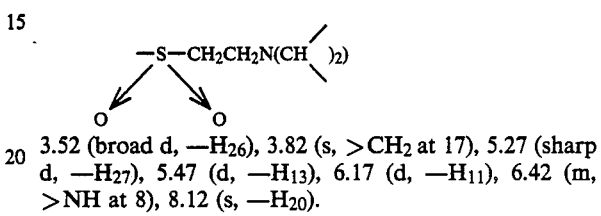

3.52 (broad d, —H$_{26}$), 3.82 (s, >CH$_2$ at 17), 5.27 (sharp d, —H$_{27}$), 5.47 (d, —H$_{13}$), 6.17 (d, —H$_{11}$), 6.42 (m, >NH at 8), 8.12 (s, —H$_{20}$).

The present invention also provides pharmaceutical compositions comprising a product of formula (I), in the form of the free base or of an addition salt with a pharmaceutically acceptable acid, in combination with either (1) one or more diluents or adjuvants which are compatible therewith and pharmaceutically acceptable; or (2) pristinamycin II$_A$ or preferably a soluble derivative of pristinamycin II$_B$ of general formula (VII). The medicinal compositions according to the invention can be used parenterally, orally, rectally or topically, and may, if desired, contain other physiologically active ingredients.

The sterile compositions for parenteral administration are preferably aqueous or non-aqueous solutions, or suspensions or emulsions. As a solvent or vehicle, it is possible to use water, propylene glycol, a polyethylene glycol, vegetable oils, especially olive oil, injectable organic esters, e.g. ethyl oleate, or other suitable organic solvents. These compositions can also contain additives, especially wetting agents, tonicity-adjusting agents, emulsifiers, dispersants and stablizers. The sterilization may be carried out in several ways, e.g. by aseptic filtration, incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules which contain, in addition to the active product, excipients such as cocoa butter, semi-synthetic glycerides or polyethylene glycols.

As solid compositions for oral administration, tablets, pills, powders or granules may be used. In these compositions, the active product according to the invention (where appropriate, in combination with another pharmaceutically acceptable product) is mixed with one or more inert diluents or additives such as sucrose, lactose or starch. These compositions can also contain substances other than diluents, e.g. a lubricant such as magnesium stearate.

As liquid compositions for oral administration, emulsions which are pharmaceutically acceptable, solutions, suspensions, syrups, and elixirs containing inert diluents such as water or liquid paraffin may be used. These compositions can also contain substances other than diluents, eg. wetting, sweetening or flavouring products.

The compositions for topical administration can be e.g. creams, ointments, lotions, eye lotions, mouthwashes, nasal drops or aerosols.

In human therapy, the products according to the invention are especially useful in the treatment of infections of bacterial origin. The doses depend on the effect sought and the duration of the treatment. For an adult, they are generally between 2000 and 4000 mg per day parenterally, especially intravenously or by slow perfusion.

In general, the medical practitioner will determine the dosage which he judges to be the most suitable according to the age, weight and all other factors specific to the subject to be treated.

The examples which follow illustrate compositions according to the invention.

EXAMPLE A

An injectable solution for perfusion containing 5 g/l of active product and having the following composition is prepared according to the usual technique:
5δ-[(3S)-3-quinuclidinyl]thiomethyl pristinamycin $I_A$: 5 g
0.1N aqueous hydrochloric acid solution: 49 cc
distilled water: qs 1000 cc.

EXAMPLE B

An injectable solution for perfusion containing 1 g/l of active mixture and having the following composition is prepared according to the usual technique:
5δ-[(3S)-3-quinuclidinyl]thiomethylpristinamycin $I_A$: 0.4 g
26-[(2-diethylaminoethyl)sulphonyl]pristinamycin $II_B$, isomer A: 0.6 g
0.1N aqueous hydrochloric acid solution. 12.6 cc
distilled water: 1000 cc.

EXAMPLE C

An injectable solution for perfusion containing 1 g/l of active mixture and having the following composition is prepared according to the usual technique:
5δ-[(3R)-3-quinuclidinyl]thiomethylpristinamycin $I_A$: 0.4 g
26-[(2-diisopropylaminoethyl)sulphonyl]pristinamycin $II_B$, isomer A: 0.6 g
0.1N aqueous hydrochloric acid solution: 12.3 cc
distilled water: qs 1000 cc.

EXAMPLE D

An injectable solution for perfusion containing 1 g/l of active mixture and having the following composition is prepared according to the usual technique:
5δ-[(3-quinuclidinyl)thiomethyl]pristinamycin $I_A$: 0.4 g
26-[(2-diethylaminopropyl)sulphinyl]pristinamycin $II_B$, isomer A: 0.6 g
0.1N aqueous hydrochloric acid solution: 12.7 cc
distilled water: qs 1000 cc.

We claim:

1. A synergistin of the formula:

in which Y is hydrogen or dimethylamino and R is 3- or 4-quinclidinyl, in the form of an isomer or a mixture thereof, and its pharmaceutically acceptable salts.

2. A synergistin according to claim 1 which is 5δ-[(3S)-3-quinuclidinyl]thiomethyl pristinamycin $I_A$, and its pharmaceutically acceptable salts.

3. A synergistin according to claim 1 which is 5δ-[(3R)-3-quinuclidinyl]-thiomethyl pristinamycin $I_A$, and its pharmaceutically acceptable salts.

4. A synergistin according to claim 1 which is 5δ-[(3S)-3-quinuclidinyl]thiomethyl virginiamycin S, and its pharmaceutically acceptable salts.

5. A synergistin according to claim 1 which is 5δ-[(3R)-3-quinuclidinyl]-thiomethyl virginiamycin S, and its pharmaceutically acceptable salts.

6. A pharmaceutical composition useful in the treatment of infections of bacterial origin which contains an effective amount of at least one synergistin as claimed in claim 1, in combination with one or more diluents or adjuvants which are compatible therewith and pharmaceutically acceptable.

7. A pharmaceutical composition useful in the treatment of infections of bacterial origin which contains an effective amount of at least one synergistin as claimed in claim 1 in combination with a synergistic amount of a pristinamycin $II_A$ or a soluble derivative of pristinamycin $II_B$ of formula:

in which $R_1$ denotes
(1) an alkylthio radical containing 1 to 5 carbon atoms, substituted by
  (i) one or two alkylamino or dialkylamino radicals in which each alkyl contains 1 to 5 carbon atoms, and, in a said dialkylamino radical, the two alkyls can form, together with the nitrogen atom to which they are attached, a saturated heterocyclic system chosen from 1-pyrrolidinyl, piperidino, 1-azetidinyl, 1-azepinyl, morpholino, thiomorpholino and 1-piperazinyl (unsubstituted or substituted by alkyl of 1 to 5 carbon atoms); or alternatively
(ii) a 2- or 3-pyrrolidinyl, 2-, 3- or 4-piperidyl, 2- or 3-azetidinyl or 2-, 3- or 4-azepinyl radical;
(2) a radical of formula:

Het—S— in which Het denotes a 3-pyrrolidinyl, 3- or 4-piperidyl, 3-azetidinyl or 3- or 4-azepinyl radical, unsubstituted or substituted by alkyl of 1 to 5 carbon atoms;
(3) a dialkylamino radical in which each alkyl contains 1 to 10 carbons and the two alkyls can be joined to form, together with the nitrogen atom to which they are attached, a saturated heterocyclic system chosen from 1-pyrrolidinyl, piperidino, 1-azetidinyl, 1-azepinyl, morpholino, thiomorpholino and 1-piperazinyl (unsubstituted or substituted by alkyl of 1 to 5 carbon atoms); or
(4) a radical of formula:

$R_2$—S—
   $(O)_n$ in which $R_2$ denotes
either a heterocyclic radical chosen from 3-azetidinyl, 3-pyrrolidinyl, 3- or 4-piperidyl, or 3- or 4-azepinyl which is unsubstituted or substituted by alkyl of 1 to 10 carbon atoms;
or an alkyl chain containing 2 to 4 carbon atoms and substituted by 1 or 2 radicals chosen from phenyl, cycloalkylamino containing 3 to 6 ring atoms and N-alkyl-N-cycloalkylamino containing 1 to 10 carbon atoms in the alkyl and having 3 to 6 ring atoms, alkylamino of 1 to 10 carbon atoms, dialkylamino of 1 to 10 carbon atoms in each alkyl, or di-alkylcarbamoyloxy of 1 to 10 carbon atoms in each alkyl (the alkyl portions of the latter 2 radicals optionally being able to form, with the nitrogen atom to which they are attached, a heterocyclic radical chosen from 1-azetidinyl, 1-pyrrolidinyl, piperidino, 1-azepinyl, morpholino, thiomorpholino in the sulphoxide or sulphone state, 1-piperazinyl, 4-alkyl-1-piperazinyl having 1 to 10 carbon atoms in the alkyl, N-alkyl-1-homopiperazinyl having 1 to 10 carbon atoms in the alkyl, or 1-imidazolyl, or substituted by one or more heterocyclic radicals chosen from 2-azetidinyl, 2-pyrrolidinyl, 2-piperidyl, 2-azepinyl, piperazinyl, 4-alkyl-piperazinyl having 1 to 10 carbons in the alkyl, quinolyl, isoquinolyl, or imidazolyl, the said radicals being unsubstituted or substituted by alkyl of 1 to 10 carbon atoms, and the said heterocyclic radicals being attached to the chain on which they are carried via a carbon atom, with the proviso that at least one of the substituents carried by the above alkyl chain is a nitrogen-containing substituent capable of forming salts;
(iii) or a [(S)-1-methyl-2-pyrrolidinyl]methyl radical and n is 1 or 2, the alkyl radicals mentioned above being linear or branched;
the said pristinamycin being, where appropriate, in the form of an isomer or mixture thereof and optionally in the form of an acid addition salt.

* * * * *

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Title page, abstract, delete the structure identified as Formula I and substitute:

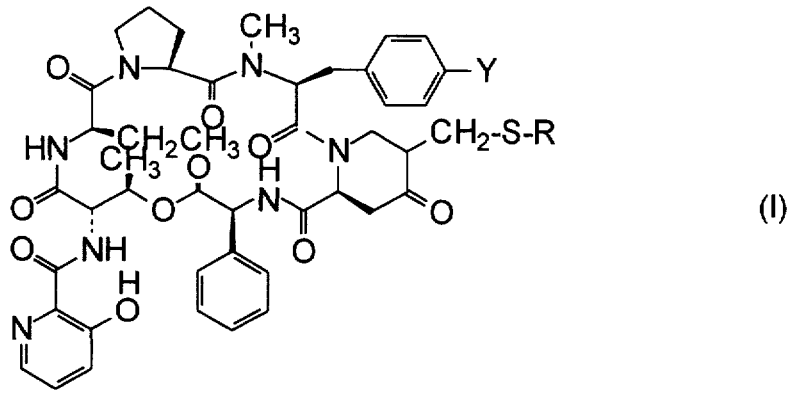

(I)

Signed and Sealed this

Seventh Day of July, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Column 1, delete Formula I and substitute

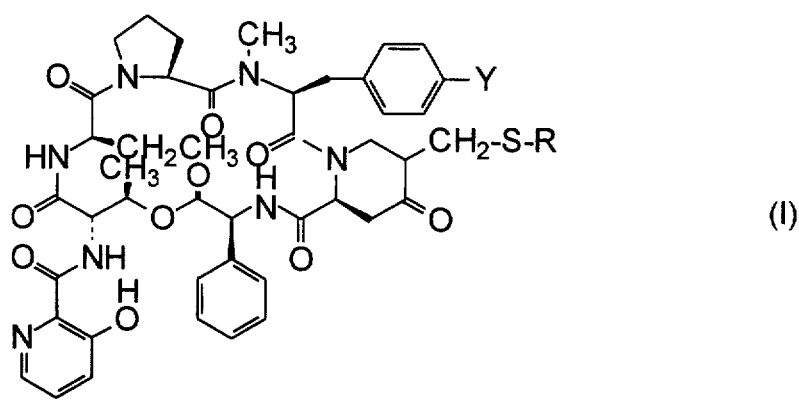

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Column 1, delete Formula III and substitute

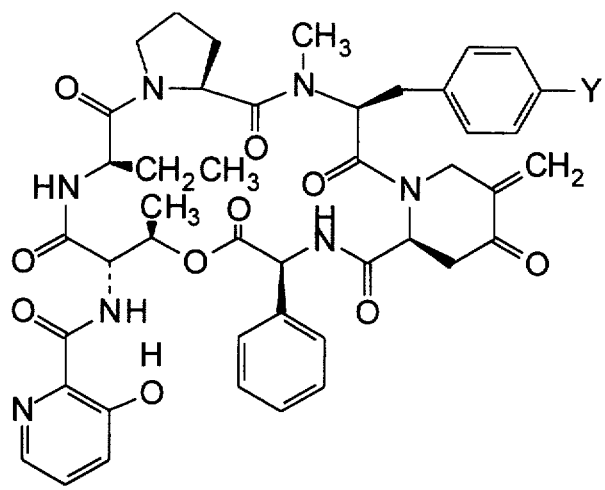

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Column 7, delete Formula XII and substitute

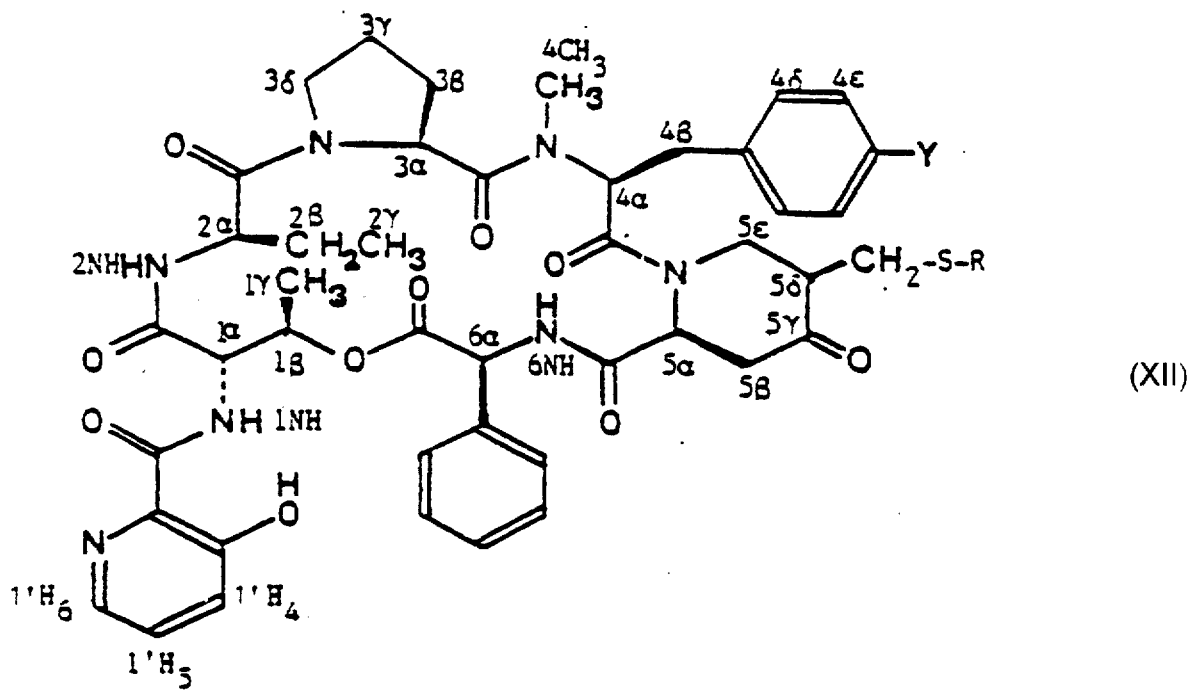

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Column 10, delete the first formula appearing between lines 37-45 and substitute

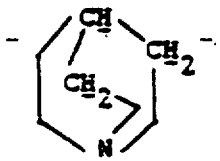

UNITED STATES PATENT AND TRADEMARK OFFICE
CERTIFICATE OF CORRECTION

PATENT NO. : 4,798,827

DATED : January 17, 1989

INVENTOR(S) : Jean-Claude Barriere et al.

It is certified that error appears in the above-indentified patent and that said Letters Patent is hereby corrected as shown below:

Column 34, claim 1, delete the formula appearing between lines 1-17 and substitute

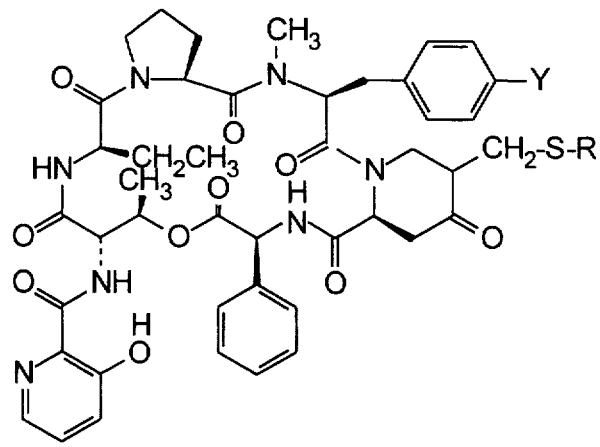

UNITED STATES PATENT AND TRADEMARK OFFICE

(12)      CERTIFICATE EXTENDING PATENT TERM
UNDER 35 U.S.C. § 156

| | | |
|---|---|---|
| (68) | PATENT NO. | : 4,798,827 |
| (45) | ISSUED | : January 17, 1989 |
| (75) | INVENTOR | : Jean-Claude Barriere, et al. |
| (73) | PATENT OWNER | : Aventis Pharma S.A. |
| (95) | PRODUCT | : SYNERCID® (quinupristin and dalfopristin) |

This is to certify that an application under 35 U.S.C. § 156 has been filed in the United States Patent and Trademark Office, requesting extension of the term of U.S. Patent No. 4,798,827 based upon the regulatory review of the product SYNERCID® (quinupristin and dalfopristin)(NDA 50-748) by the Food and Drug Administration. Since it appears that the requirements of the law have been met, this certificate extends the term of the patent for the period of

(94)                  1,770 days from May 21, 2007, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 2004.

JAMES E. ROGAN
Under Secretary of Commerce for Intellectual Property and Director of the United States Patent and Trademark Office